United States Patent
Ogasawara et al.

(10) Patent No.: US 12,178,570 B2
(45) Date of Patent: Dec. 31, 2024

(54) MONITORING SYSTEM, MONITORING METHOD, AND MONITORING PROGRAM

(71) Applicant: Nippon Telegraph and Telephone Corporation, Tokyo (JP)

(72) Inventors: Takayuki Ogasawara, Tokyo (JP); Kenichi Matsunaga, Tokyo (JP); Rieko Sato, Tokyo (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 105 days.

(21) Appl. No.: 17/774,402

(22) PCT Filed: Nov. 28, 2019

(86) PCT No.: PCT/JP2019/046632
§ 371 (c)(1),
(2) Date: May 4, 2022

(87) PCT Pub. No.: WO2021/106162
PCT Pub. Date: Jun. 3, 2021

(65) Prior Publication Data
US 2022/0354387 A1    Nov. 10, 2022

(51) Int. Cl.
*A61B 5/11* (2006.01)
*A61B 5/00* (2006.01)
(Continued)

(52) U.S. Cl.
CPC .......... *A61B 5/1128* (2013.01); *A61B 5/0077* (2013.01); *A61B 5/1117* (2013.01);
(Continued)

(58) Field of Classification Search
CPC ... A61B 5/0013; A61B 5/0077; A61B 5/1113; A61B 5/1117; A61B 5/1118;
(Continued)

(56) References Cited

U.S. PATENT DOCUMENTS

| | | | | |
|---|---|---|---|---|
| 2002/0033960 A1* | 3/2002 | Kazami | ............. | H04N 1/00458 358/1.14 |
| 2003/0231787 A1* | 12/2003 | Sumi | ............... | G08B 13/19686 382/103 |

(Continued)

FOREIGN PATENT DOCUMENTS

| | | |
|---|---|---|
| JP | 2009003486 A | 1/2009 |
| JP | 2017068422 A | 4/2017 |

(Continued)

OTHER PUBLICATIONS

Kimura, K, "Handbook for electric care bed for home care," Medical and Nursing Bed Safety Promotion Council, Feb. 20, 2006, pp. 1-40.

(Continued)

*Primary Examiner* — Peter D Le
(74) *Attorney, Agent, or Firm* — Slater Matsil, LLP

(57) ABSTRACT

A monitoring system includes a sensor data acquisition device configured to acquire information on an activity of a user; a data analyzer configured to analyze the acquired information on the activity of the user and detect occurrence of an abnormality in the activity of the user; an imaging controller configured to instruct an imaging terminal device that captures an image of the activity of the user to start capturing an image of the user and record imaging data in a case where the occurrence of the abnormality is detected by the data analyzer; an imaging data acquisition device configured to acquire the imaging data recorded by the imaging terminal device; a data storage device configured to store the imaging data acquired by the imaging data acquisition device; and an output device configured to output the imaging data.

16 Claims, 23 Drawing Sheets

(51) Int. Cl.
    *G08B 21/04*         (2006.01)
    *H04N 7/18*          (2006.01)
    *H04N 23/60*        (2023.01)

(52) U.S. Cl.
    CPC ........ *A61B 5/1118* (2013.01); *G08B 21/0492* (2013.01); *H04N 7/183* (2013.01); *H04N 7/188* (2013.01); *H04N 23/60* (2023.01); *A61B 5/0013* (2013.01)

(58) Field of Classification Search
    CPC ...... A61B 5/1128; G06V 20/52; G06V 40/20; G08B 21/0476; G08B 21/0492; H04N 23/60; H04N 7/183; H04N 7/188
    See application file for complete search history.

(56) References Cited

U.S. PATENT DOCUMENTS

| | | | |
|---|---|---|---|
| 2006/0079998 A1* | 4/2006 | Yoshikawa | G08B 13/19647 |
| | | | 700/245 |
| 2006/0161686 A1* | 7/2006 | Mossakowski | H04N 19/436 |
| | | | 707/E17.031 |
| 2007/0031141 A1* | 2/2007 | Tanaka | G02B 26/004 |
| | | | 396/287 |
| 2007/0098381 A1* | 5/2007 | Oshima | H04N 23/68 |
| | | | 348/E5.046 |
| 2008/0212421 A1* | 9/2008 | Kitagawa | H04N 5/76 |
| | | | 369/47.12 |
| 2009/0198374 A1* | 8/2009 | Tsai | G16H 40/67 |
| | | | 700/245 |
| 2009/0244404 A1* | 10/2009 | Park | H04N 19/597 |
| | | | 348/739 |
| 2010/0268304 A1* | 10/2010 | Matos | G16H 40/63 |
| | | | 607/60 |
| 2012/0314901 A1* | 12/2012 | Hanson | G16H 40/67 |
| | | | 600/595 |
| 2013/0294651 A1* | 11/2013 | Zhou | G06V 40/28 |
| | | | 382/103 |
| 2014/0146182 A1* | 5/2014 | Endo | G06T 7/254 |
| | | | 348/169 |
| 2014/0147092 A1* | 5/2014 | Liu | H04M 1/656 |
| | | | 455/414.1 |
| 2014/0201844 A1* | 7/2014 | Buck | G06F 21/554 |
| | | | 726/26 |
| 2015/0221202 A1* | 8/2015 | Russell | A61B 5/1117 |
| | | | 340/573.7 |
| 2016/0038094 A1* | 2/2016 | An | A61B 5/1118 |
| | | | 600/595 |
| 2016/0183847 A1* | 6/2016 | Pae | A61B 5/1117 |
| | | | 600/595 |
| 2017/0185082 A1* | 6/2017 | Matos | A61M 5/1723 |
| 2018/0129276 A1* | 5/2018 | Nguyen | G06F 3/0304 |
| 2018/0173974 A1* | 6/2018 | Chang | G06V 20/597 |
| 2018/0185662 A1* | 7/2018 | Foshee, Jr | A61B 5/4809 |
| 2018/0289310 A1* | 10/2018 | Girouard | A61B 5/7282 |
| 2019/0082044 A1* | 3/2019 | Melendez | H04W 4/023 |
| 2020/0120375 A1* | 4/2020 | Hamon | H04N 21/4627 |
| 2020/0412999 A1* | 12/2020 | Mori | H04N 5/9202 |
| 2022/0211290 A1* | 7/2022 | Takahashi | A61B 5/1116 |

FOREIGN PATENT DOCUMENTS

| | | |
|---|---|---|
| JP | 2017080382 A | 5/2017 |
| WO | 2018139398 A1 | 8/2018 |

OTHER PUBLICATIONS

Ogasawara et al., "The wearable material hitoe @ is applied. Rehabilitation Support Initiative take-back," NTT Technical Journal Jul. 2018, pp. 10-14.

* cited by examiner

MONITORING SYSTEM, MONITORING METHOD, AND MONITORING PROGRAM

CROSS-REFERENCE TO RELATED APPLICATIONS

This application is a national phase entry of PCT Application No. PCT/JP2019/046632, filed on Nov. 28, 2019, which application is hereby incorporated herein by reference.

TECHNICAL FIELD

The present disclosure relates to a monitoring system, a monitoring method, and a monitoring program, and particularly relates to a technique of watching over a patient in medical or nursing care.

BACKGROUND

In medical facilities or nursing facilities, various bed-related accidents such as a patient tripping over a bed and falling or falling off a bed have occurred (see NPL 1). In a case where a patient hits his or her head when he or she falls, urgent examination or surgery may be required. In a case where a patient has a possibility of physical injury due to a fall, there is a need for a means to immediately notify a healthcare professional or a caregiver in charge of the patient.

On the other hand, a system that makes it possible to monitor a patient using a sensor has been proposed for medical or nursing facilities (see NPL 2). FIG. 23 is a diagram illustrating an outline of a monitoring system of the related art disclosed in NPL 2.

As illustrated in FIG. 23, in the monitoring system of the related art, a user such as a patient puts on rehabilitation wear of a wearable device, and data of the user's cardiac potential or acceleration is acquired by the wearable device. The wear for rehabilitation is provided with a transmitter, and information on the user's cardiac potential or acceleration is transmitted from the transmitter to a relay terminal device such as a smartphone or an IoT gate.

The data of the user's cardiac potential or acceleration is stored, integrated, and analyzed by an external terminal device such as a server which is connected via a network. Based on the user's biometric information analyzed by the external terminal device, analysis results are output and a healthcare professional in charge of medical or nursing care of the user such as a doctor, a therapist, or a nurse is notified of the results through a viewer.

From the analysis results or reports which are received, a doctor, a therapist, a nurse, or the like can provide more suitable care for a user when treating or taking care of the user in charge.

However, in the monitoring system of the related art disclosed in NPL 2, it may be difficult to ascertain whether the user has actually fallen or fallen off a bed or the like and hit his or her head only with the information on cardiac potential or acceleration. On the other hand, whether the user has hit his or her head can be ascertained by installing a generally well-known monitoring camera in a rehabilitation room, a hospital room, or the like to constantly capture an image of and record the user's state. However, it is a heavy burden for the user from a psychiatric viewpoint for their daily life to be constantly recorded, and the amount of data associated with the constant image capturing and recording also increases. Thus, it has been difficult to perform monitoring with a reduced burden on the user.

CITATION LIST

Patent Literature

PTL 1: International Publication WO 2018/139398

Non Patent Literature

NPL 1: Safety Promotion Council for Medical and Home Care Bed "Electric Nursing Bed Handbook in Home Care" Feb. 20, 2006 (p. 2)

NPL 2: Takayuki Ogasawara, Kenichi Matsunaga, Hiroki Ito, Shoichi Oshima, and Masahiko Mukaino "Application for Rehabilitation Medicine Using Wearable Textile "hitoe" (trade name)", NTT Technical Journal, 2018. 7 (FIG. 3

SUMMARY

Technical Problem

The present disclosure was contrived in order to solve the above-described problems, and an object thereof is to perform monitoring with a reduced burden on a user.

Means for Solving the Problem

In order to solve the above-described problem, according to the present disclosure, a monitoring system includes: a sensor data acquisition unit configured to acquire information on an activity of a user; a data analysis unit configured to analyze the acquired information on the activity of the user and detect occurrence of an abnormality in the activity of the user; an imaging control unit configured to instruct an imaging terminal device that captures an image of the activity of the user to start capturing an image of the user and record imaging data in a case where the occurrence of the abnormality is detected by the data analysis unit; an imaging data acquisition unit configured to acquire the imaging data recorded by the imaging terminal device; a data storage unit configured to store the imaging data acquired by the imaging data acquisition unit; and an output unit configured to output the imaging data, wherein the information on the activity of the user includes an acceleration of the user.

In order to solve the above-described problem, according to the present disclosure, a monitoring system includes: a sensor data acquisition unit configured to acquire information on an activity of a user; a data analysis unit configured to analyze the acquired information on the activity of the user and detect whether an abnormality has occurred in the activity of the user; an imaging control unit configured to instruct an imaging terminal device that has started capturing an image of the user and recording imaging data in advance to erase the imaging data that has already been recorded in a case where the occurrence of the abnormality is not detected by the data analysis unit; an imaging data acquisition unit configured to acquire the imaging data recorded by the imaging terminal device in a case where the occurrence of the abnormality is detected by the data analysis unit; a data storage unit configured to store the imaging data acquired by the imaging data acquisition unit; and an output unit configured to output the imaging data, wherein the information of the activity of the user includes an acceleration of the user.

In order to solve the above-described problem, according to the present disclosure, a monitoring system includes: a sensor terminal device configured to output information on an activity of a user which is measured by a sensor worn by the user to outside; a relay terminal device configured to receive the information on the activity of the user which is output from the sensor terminal device and output the received information on the activity of the user to outside; an external terminal device configured to receive the information on the activity of the user which is output from the sensor terminal device or the relay terminal device and cause a storage device to store the received activity information; and an imaging terminal device configured to start capturing an image of the user in accordance with an instruction from outside, record imaging data, and transmit the imaging data to the external terminal device, wherein at least any of the sensor terminal device, the relay terminal device, and the external terminal device includes a sensor data acquisition unit configured to acquire the information on the activity of the user, a data analysis unit configured to analyze the acquired information on the activity of the user and detect occurrence of an abnormality in the activity of the user, an imaging control unit configured to instruct the imaging terminal device to start capturing an image of the user and record imaging data in a case where the occurrence of the abnormality is detected by the data analysis unit, an imaging data acquisition unit configured to acquire the imaging data recorded by the imaging terminal device, a data storage unit configured to store the imaging data acquired by the imaging data acquisition unit, and an output unit configured to output the imaging data, and the information of the user includes an acceleration of the user.

In order to solve the above-described problem, according to the present disclosure, a monitoring method includes: acquiring information on an activity of a user; analyzing the acquired information on the activity of the user and detecting occurrence of an abnormality in the activity of the user; instructing an imaging terminal device that captures an image of the activity of the user to start capturing an image of the user and record imaging data in a case where the occurrence of the abnormality is detected; acquiring the imaging data recorded by the imaging terminal device; storing the acquired imaging data in a data storage unit; and outputting the imaging data, wherein the information on the activity of the user includes an acceleration of the user.

In order to solve the above-described problem, according to the present disclosure, a monitoring program causes a computer to execute: acquiring information on an activity of a user;

analyzing the acquired information on the activity of the user and detecting occurrence of an abnormality in the activity of the user; instructing an imaging terminal device that captures an image of the activity of the user to start capturing an image of the user and record imaging data in a case where the occurrence of the abnormality is detected; acquiring the imaging data recorded by the imaging terminal device; storing the acquired imaging data in a data storage unit; and outputting the imaging data, wherein the information on an activity of a user includes an acceleration of the user.

Effects of Embodiments of the Invention

According to the present disclosure, when the information on the user's activity is analyzed and the occurrence of an abnormality in the user's activity is detected, the imaging terminal device is instructed to start capturing an image of the user and start recording the imaging data to acquire the recorded imaging data, and thus it is possible to perform monitoring with a reduced burden on the user.

DETAILED DESCRIPTION OF ILLUSTRATIVE EMBODIMENTS

Hereinafter, preferred embodiments of the present disclosure will be described in detail with reference to FIGS. 1 to 22.

Outline of Embodiments of the Invention

Figure 7:
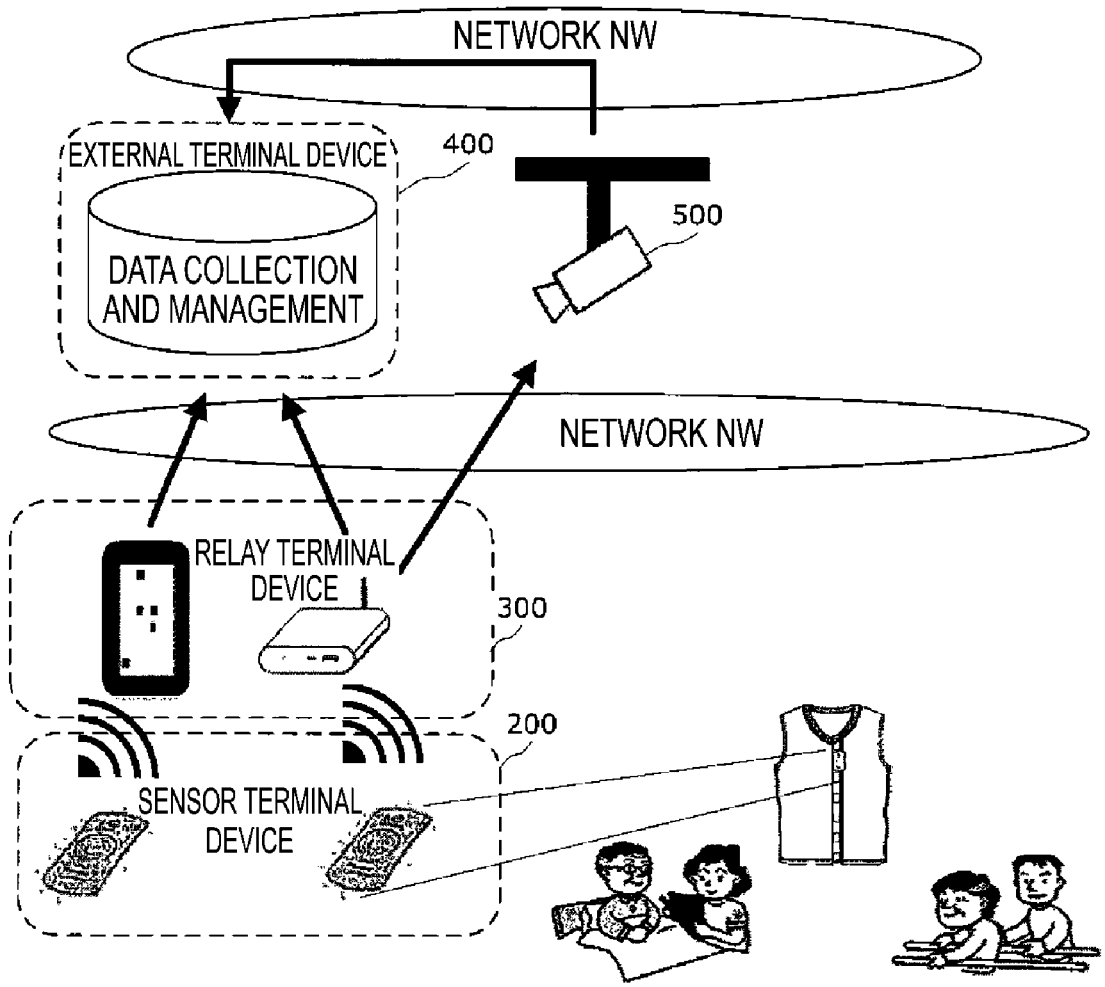
FIG. 7 is a diagram illustrating an outline of the configuration example of the monitoring system according to the first embodiment.

First, an outline of a monitoring system according to an embodiment of the present disclosure will be described. As illustrated in FIG. 7, the monitoring system according to the present embodiment detects that a user undergoing rehabilitation at a nursing facility, a patient in hospital, or the like has fallen, for example, while sleeping at night or while being active alone in the daytime. In addition, when a user's fall is detected, the monitoring system according to the present embodiment causes an imaging terminal device such as a camera disposed in advance in a rehabilitation room, a hospital room, or the like where the user is located to capture an image of the user and record imaging data.

The imaging terminal device captures an image of the user's state in accordance with the detection of an abnormality in the user's activity including the user's fall, so that the monitoring system can acquire imaging data including a state of the user falling, for example, his or her head or body hitting the floor.

Meanwhile, the term "fall over" refers to case in which a user falls on one plane, and the term "fall off" refers to a case in which a user falls to a lower plane. For example, "fall over" includes a case where a user's body unintentionally stumbles on the floor or ground and the user falls to the floor, and "fall off" includes a case where a user unintentionally falls from a high place to a low place.

In addition, in the present embodiment, falling is described as a specific example of an abnormality occurring in a user's activity, and the user's activity is the user's physical movement. Both falling over and falling off something pose a high risk of the user hitting his or her head or the like on the floor or the like. Thus, falling is an occurrence of an abnormality in a user's activity that a healthcare professional or the like in charge of the user needs to immediately be aware of. In the following embodiments, falling over and falling off something may be described synonymously.

First Embodiment

Figure 1:
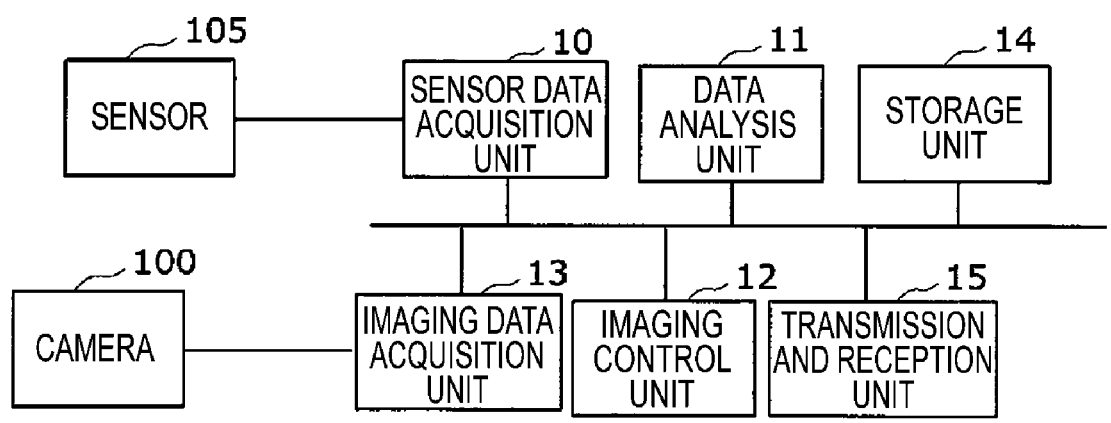
FIG. 1 is a block diagram illustrating a functional configuration of a monitoring system according to a first embodiment of the present disclosure.

First, an outline of a configuration of a monitoring system according to a first embodiment of the present disclosure will be described. FIG. 1 is a block diagram illustrating a functional configuration of a monitoring system.
Functional Block of Monitoring System The monitoring system includes a sensor data acquisition unit 10 that acquires data from a sensor 105, a data analysis unit 11, an imaging control unit 12, an imaging data acquisition unit 13 that acquires imaging data from a camera 100, a storage unit (data storage unit) 14, and a transmission and reception unit (output unit) 15.

The sensor data acquisition unit 10 acquires information on the user's activity measured by the sensor 105. The information on the user's activity includes information indicating the movement of the user's body, for example, an acceleration. The sensor data acquisition unit 10 acquires, for example, the user's acceleration signal measured by the sensor 105 constituted by an acceleration sensor worn by the user. The sensor data acquisition unit 10 converts the acquired analog acceleration signal into a digital signal at a predetermined sampling rate. In addition, the sensor data acquisition unit 10 can perform known signal processing as necessary, such as noise removal or amplification of the acceleration signal. Time-series data of the activity information acquired by the sensor data acquisition unit 10 is stored in the storage unit 14 to be described later.

The sensor data acquisition unit 10 can also acquire the user's electrocardiac signal as the information on the user's activity in addition to the acceleration.

Figure 2:
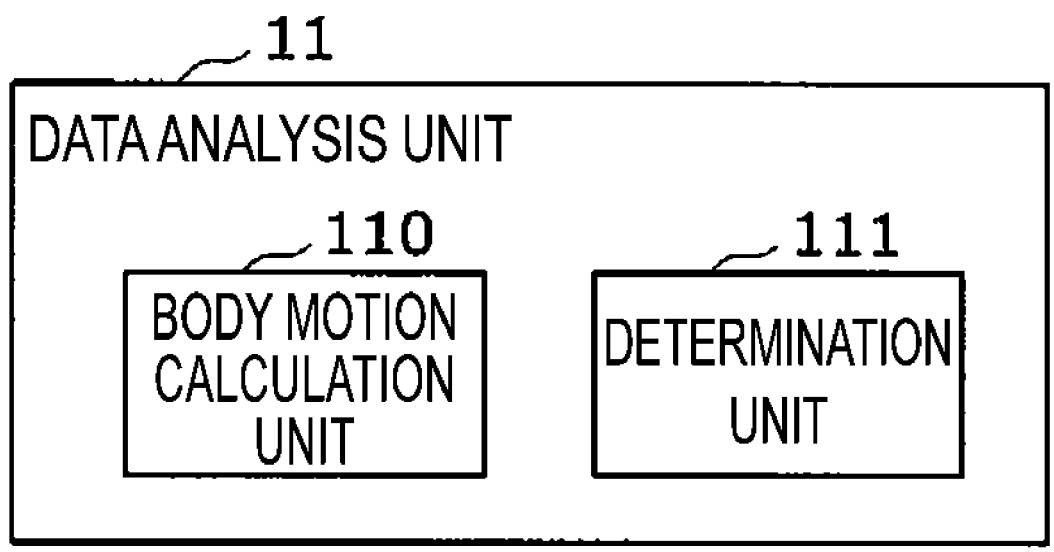
FIG. 2 is a block diagram illustrating a configuration of a data analysis unit according to the first embodiment.

The data analysis unit 11 analyzes the information on the user's activity acquired by the sensor data acquisition unit 10, and detects the occurrence of an abnormality in the user's activity. As illustrated in FIG. 2, the data analysis unit 11 includes a body motion calculation unit no and a determination unit (first determination unit) 111.

The body motion calculation unit 110 calculates the user's body motion from the information on the user's activity acquired by the sensor data acquisition unit 10. For example, the norm of the user's acceleration measured by the sensor 105 constituted by a 3-axis acceleration sensor can be used as the body motion. More specifically, the body motion calculation unit no calculates the norm of an acceleration value of one axis, the norm of acceleration values of two axes, or the norm of acceleration values of three axes of acceleration on any of 3 axes as the user's body motion.

The determination unit 111 determines that an abnormality has occurred in the user's activity in a case where the value of the user's body motion calculated by the body motion calculation unit no satisfies a setting criterion. As the setting criterion, the value of body motion or the like according to a specific activity that is desired to be detected can be used. For example, in a case where a sleeping user falling off a bed is desired to be detected, or a case where a walking user falling is desired to be detected, the setting criterion is provided based on the value of the user's body motion or the like corresponding to each of sleeping, walking, and falling examined in advance. Hereinafter, the setting criterion used in a case where a sleeping user falling off a bed is detected will be described.

Figure 3:
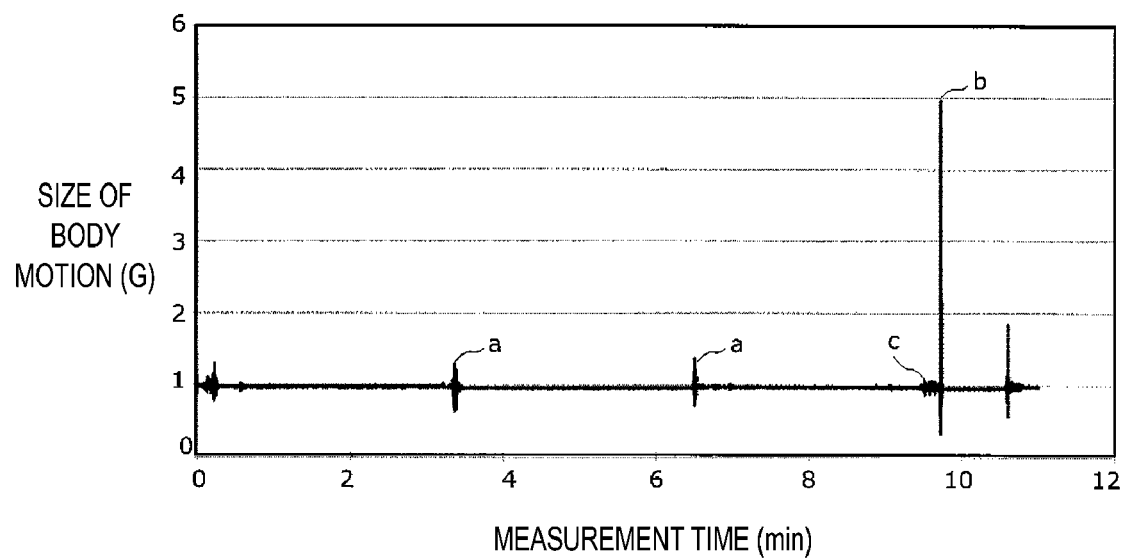
FIG. 3 is a diagram illustrating the data analysis unit according to the first embodiment.

FIG. 3 is a diagram illustrating a body motion [G] obtained by calculating the norm of the acceleration value of a subject sleeping in a bed. The horizontal axis in FIG. 3 indicates a measurement time [minutes]. In FIG. 3, "a" indicates the value of body motion when the subject rolls over. In addition, "b" indicates the value of body motion when the subject falls off the bed.

As illustrated in FIG. 3, the body motion of the sleeping subject is mainly about 1 [G], and the body motion increases when he or she rolls over but does not exceed 2 [G]. On the other hand, the body motion when the subject falls off the bed has a value exceeding 5 [G]. From data of such values of body motion, as the setting criterion, for example, in a case where the value of the user's body motion exceeds 2 [G], the determination unit 111 can consider that an abnormality has occurred in the user's activity, that is, a fall has occurred for the user.

In this way, in the present embodiment, in a case where the value of the user's body motion exceeds 2 [G], the determination unit 111 satisfies the setting criterion and determines that the user has fallen.

Meanwhile, in a case where the same setting criterion as described above is satisfied, the determination unit 111 can also determine that the user has fallen down. In addition, it may be configured to determine an abnormality that occurs in the user's activity not only by an event in which the value of the user's body motion becomes extremely large but also by an event in which, for example, the value of the user's body motion changes from a predetermined value to 1 [G] which indicates a stationary state. In this case, for example, the sudden stillness of the user who was performing a rehabilitation exercise is detected as the occurrence of an abnormality in the user's activity.

Next, when the occurrence of an abnormality in the user's activity is detected by the data analysis unit 11, the imaging control unit 12 instructs the camera 100 to start capturing an image of the user and record imaging data. The configuration of the camera 100 will be described later, but in the present embodiment, the camera 100 is disposed in advance at a position where the user performs activity. For example, the camera 100 is installed in advance in a room in which the user is located, and its operation is controlled by the imaging control unit 12.

In addition, when a preset period elapses in a case where the camera 100 is instructed to start capturing an image of the user and record the imaging data, the imaging control unit 12 can instruct the camera 100 to end the image capturing. Alternatively, the image capturing time can also be limited by a timer built into the camera 100 to be described later.

When the imaging control unit 12 instructs the camera to start capturing an image of the user, the camera 100 captures an image of an abnormality that occurs in the user's activity. For example, from a point in time when the user falls off the bed while sleeping, images of a series of states of the user falling to and hitting the floor are captured by the camera 100 and recorded in a memory.

The imaging data acquisition unit 13 acquires the imaging data captured and recorded by the camera 100.

The storage unit 14 stores the imaging data acquired by the imaging data acquisition unit 13.

The transmission and reception unit 15 sends out (outputs) the imaging data stored in the storage unit 14 to, for example, an external terminal device.

Computer Configuration of Monitoring System

Next, an example of a computer configuration for implementing the monitoring system having the above-mentioned functions will be described with reference to FIG. 4.

Figure 4:
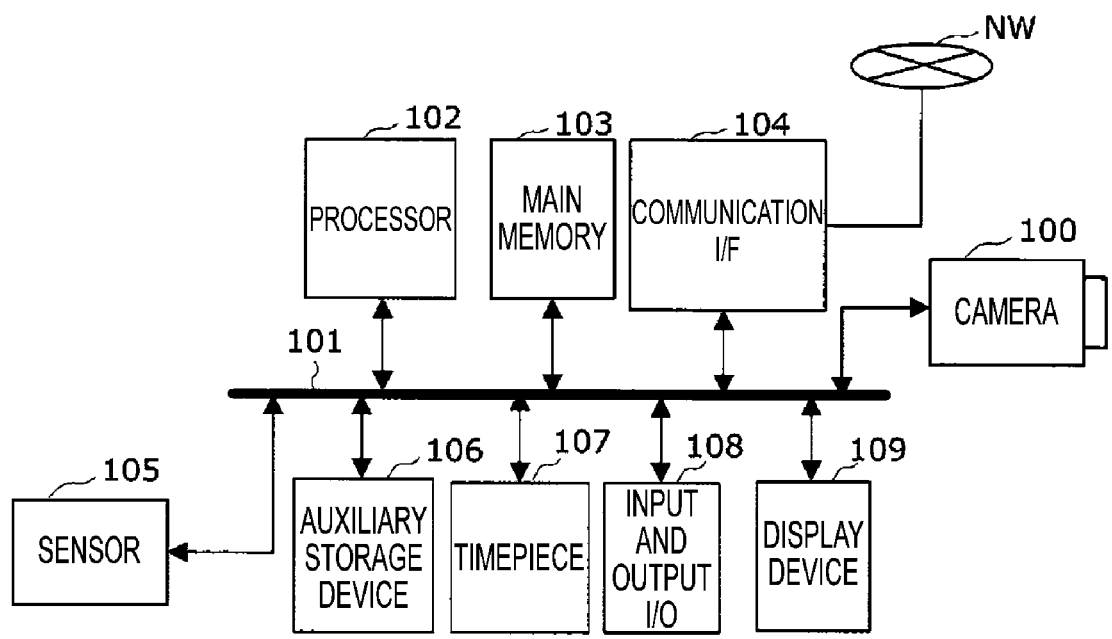
FIG. 4 is a block diagram illustrating an example of a computer configuration for realizing the monitoring system according to the first embodiment.

As illustrated in FIG. 4, the monitoring system can be implemented by, for example, a computer including a processor 102, a main memory 103, a communication I/F 104, an auxiliary storage device 106, a timepiece 107, and an input and output I/O 108 which are connected to each other via a bus 101 and a program for controlling these hardware resources. The monitoring system is configured such that, for example, the sensor 105, a display device 109, and the camera 100 which are provided externally are connected to each other via the bus 101.

A program for the processor 102 to perform various types of control or calculations is stored in the main memory 103 in advance. The processor 102 and the main memory 103 realize each function of the monitoring system including the data analysis unit 11 and the imaging control unit 12 illustrated in FIGS. 1 and 2.

The communication I/F 104 is an interface circuit for communicating with various external electronic devices via a communication network NW.

The communication I/F 104 is obtained by using a communication control circuit and an antenna corresponding to wireless data communication standards such as, for example, 3G, 4G, 5G, a wireless LAN, Bluetooth (trade name), or Bluetooth Low Energy. The communication I/F 104 realizes the sensor data acquisition unit 10, the imaging data acquisition unit 13, and the transmission and reception unit 15 which are described in FIG. 1.

The sensor 105 is constituted by, for example, a 3-axis acceleration sensor. The sensor 105 can further include, for example, an electrocardiograph, a sphygmomanometer, a pulse rate meter, a respiration sensor, a thermometer, a brainwave sensor, or the like.

The auxiliary storage device 106 is constituted by a readable and writable storage medium and a drive device for reading and writing various types of information such as a program or data to and from the storage medium. A semiconductor memory such as a hard disk or a flash memory can be used as a storage medium in the auxiliary storage device 106.

The auxiliary storage device 106 has a storage area for storing the information on the user's activity measured by the sensor 105 and a program storage area for storing a program for the monitoring system to perform an analysis process on the activity information or a monitoring program. The auxiliary storage device 106 realizes the storage unit 14 described in FIG. 1. Further, for example, it may have a backup area for backing up the above-described data, programs, or the like.

The timepiece 107 is constituted by a built-in timepiece or the like built into a computer, and clocks a time. Alternatively, the timepiece 107 may acquire time information from a time server (not illustrated). The time information obtained by the timepiece 107 is used for sampling an acceleration signal or the like.

The input and output I/O 108 is constituted by an I/O terminal for inputting a signal from an external device such as the camera 100 or outputting a signal to the external device.

The display device 109 is obtained by a liquid crystal display or the like. The display device 109 can output the imaging data.

The camera 100 can convert an optical signal into an image signal to generate a moving image or a still image. More specifically, the camera 100 has an imaging element such as a charge-coupled device (CCD) image sensor or a CMOS image sensor to form an image of light incident from an imaging region on a light receiving surface and convert it into an electrical signal. Meanwhile, the frame rate, exposure value, magnification, focus, and the like in a case where the camera 100 captures a moving image are automatically set in advance by a processor (not illustrated) included in the camera 100. As the camera 100, for example, a visible light camera, a night-vision camera, a WEB camera, or the like can be used.

In addition, the camera 100 includes a memory for recording the imaging data and the communication I/F, which are not illustrated in FIG. 4.

Monitoring Method

Figure 5:
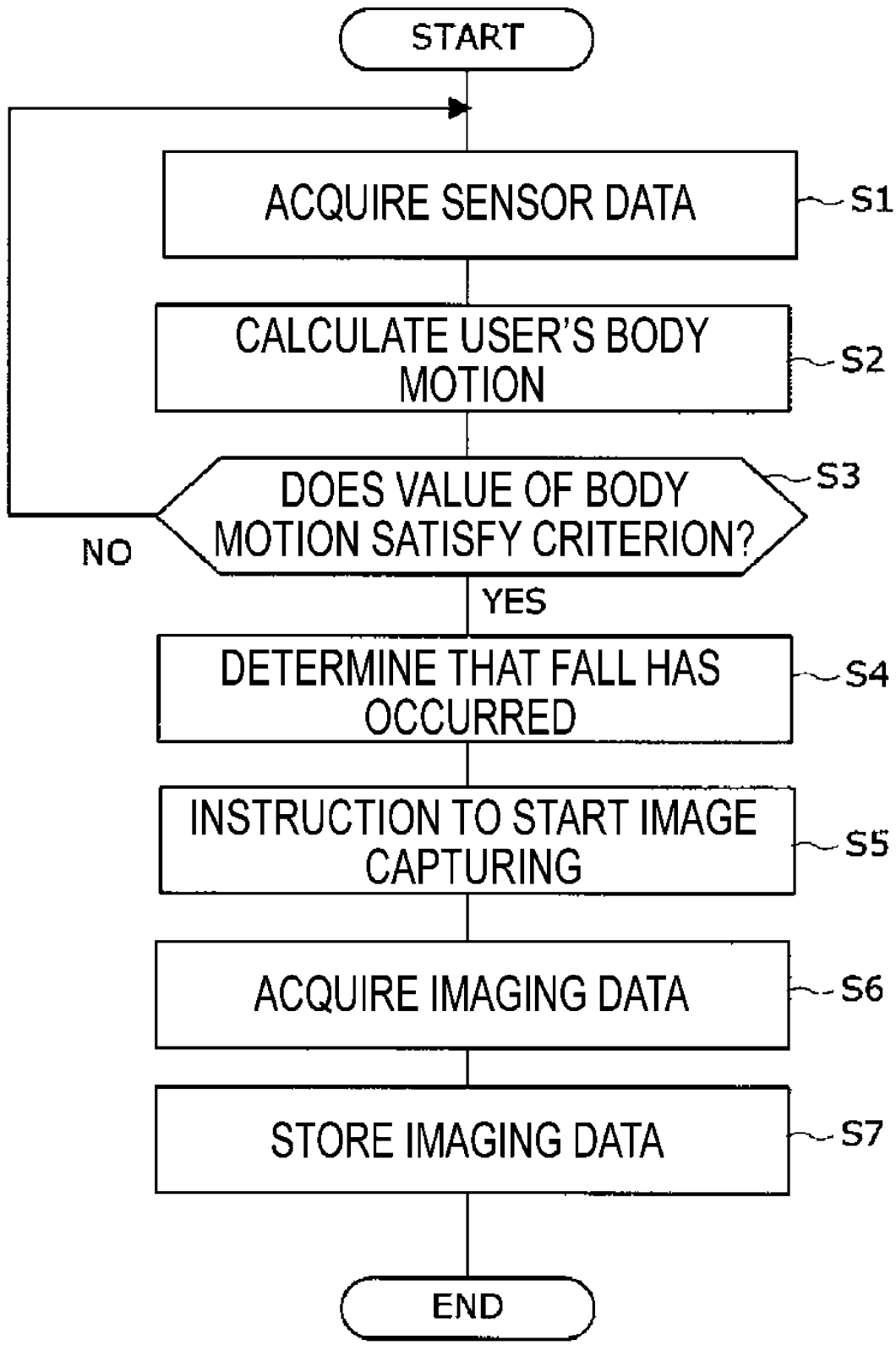
FIG. 5 is a flowchart illustrating a monitoring method according to the first embodiment.

Next, operations of the monitoring system having the above-described configuration will be described with reference to the flowchart of FIG. 5. First, the camera 100 is installed in advance in a room or the like where the user performs activities such as sleeping or rehabilitation. In addition, when the sensor 105 including a 3-axis acceleration sensor is mounted on the user in advance and the measurement of an acceleration is started as the activity information, the following processes are executed.

First, the sensor data acquisition unit 10 acquires the user's acceleration signal measured by the sensor 105 (step S1). In step S1, the sensor data acquisition unit 10 performs known signal processing such as amplification, AD conversion, or noise removal on the acquired acceleration signal which is the information on the user's activity. The acquired time-series data of the user's acceleration is stored in the storage unit 14.

Next, the body motion calculation unit no calculates the user's body motion from the user's acceleration data acquired in step S1 (step S2).

Next, in a case where the value of the user's body motion calculated in step S2 satisfies the set criterion (step S3: YES), the determination unit 111 determines that an abnormality has occurred in the user's activity, that is, the user has fallen (step S4). For example, in a case where the value of the user's body motion exceeds 2 [G], the determination unit 111 determines that a fall has occurred.

Next, when the determination unit 111 determines that the user's fall has occurred, the imaging control unit 12 instructs the external camera 100 to start capturing an image of the user and record the imaging data (step S5). Thereafter, the camera 100 starts capturing an image of the user, captures images of states from a point in time when the user falls to a time when the user hits the floor or the like, and records the imaging data in a memory.

Next, the imaging data acquisition unit 13 acquires the imaging data recorded by the camera 100 (step S6). Thereafter, the acquired imaging data is stored in the storage unit 14 (step S7). Meanwhile, the transmission and reception unit 15 can send out the imaging data stored in the storage unit 14 to an external terminal device or the like.

Specific Configuration of Monitoring System

Next, a specific configuration example of the monitoring system having the above-described configuration will be described with reference to FIGS. 6 to 8.

Figure 6:
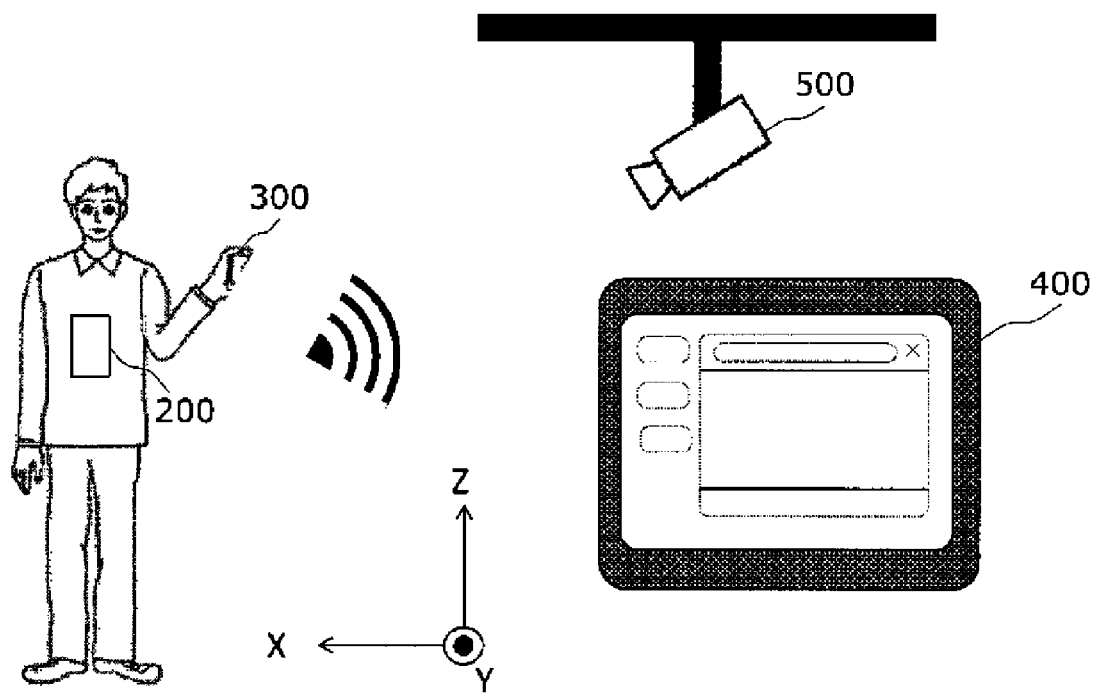
FIG. 6 is a diagram illustrating an outline of a configuration example of the monitoring system according to the first embodiment.

For example, as illustrated in FIGS. 6 and 7, the monitoring system includes a sensor terminal device 200 worn by a user who is resting in a hospital room or a user undergoing rehabilitation, a relay terminal device 300, an external terminal device 400, and an imaging terminal device 500 that captures an image of the state of the user's activity. All or any of the sensor terminal device 200, the relay terminal device 300, and the external terminal device 400 includes a function included in the monitoring system such as the data analysis unit 11 or the imaging control unit 12 described in FIGS. 1 and 2.

It is assumed below that the relay terminal device 300 includes the data analysis unit 11 and the imaging control unit 12 described in FIG. 1, and that the external terminal device 400 includes the imaging data acquisition unit 13 and the storage unit 14.

Functional Block of Sensor Terminal Device

Figure 8:
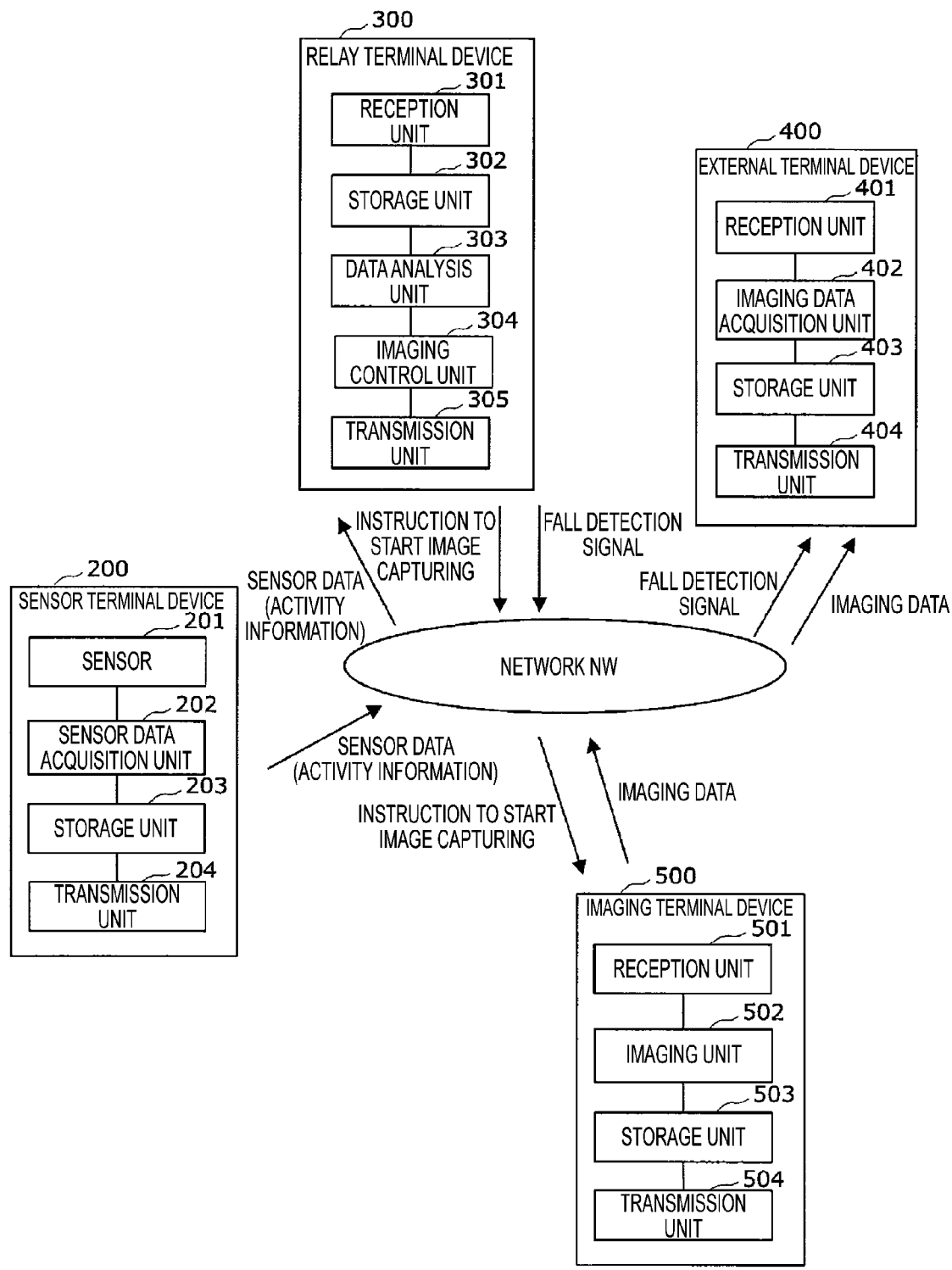
FIG. 8 is a block diagram illustrating the configuration example of the monitoring system according to the first embodiment.

As illustrated in FIG. 8, the sensor terminal device 200 includes a sensor 201, a sensor data acquisition unit 202, a storage unit 203, and a transmission unit 204. The sensor terminal device 200 is disposed on, for example, the trunk of the user's body to measure activity information. The sensor terminal device 200 transmits the measured information on the user's activity to the relay terminal device 300 via the communication network NW.

The sensor 201 is obtained by, for example, a 3-axis acceleration sensor or the like. For example, as illustrated in FIG. 6, three axes of an acceleration sensor included in the sensor 201 are configured such that the X axis is provided parallel to the horizontal direction of the body, the Y axis is provided parallel to the front-rear direction of the body, and the Z axis is provided parallel to the vertical direction of the body. The sensor 201 corresponds to the sensor 105 described in FIGS. 1 and 4.

The sensor data acquisition unit 202 acquires the information on the user's activity measured by the sensor 201. More specifically, the sensor data acquisition unit 202 performs noise removal or a sampling process on the acceleration signal which is the acquired activity information, and obtains time-series data of acceleration of a digital signal. The sensor data acquisition unit 202 corresponds to the sensor data acquisition unit 10 described in FIG. 1.

The storage unit 203 stores the time-series data of the information on the user's activity measured by the sensor 201 or the activity information of the digital signal processed and obtained by the sensor data acquisition unit 202. The storage unit 203 corresponds to the storage unit 14 (FIG. 1).

The transmission unit 204 transmits the information on the user's activity stored in the storage unit 203 to the relay terminal device 300 via the communication network NW. The transmission unit 204 includes a communication circuit for performing wireless communication corresponding to wireless data communication standards such as LTE, 3G, 4G, 5G, a wireless local area network (LAN), Bluetooth (trade name), or Bluetooth Low Energy. The transmission unit 204 corresponds to the transmission and reception unit 15 (FIG. 1).

Functional Block of Relay Terminal Device

The relay terminal device 300 includes a reception unit 301, a storage unit 302, a data analysis unit 303, an imaging control unit 304, and a transmission unit 305. The relay terminal device 300 analyzes the information on the user's activity received from the sensor terminal device 200, and detects an abnormality that has occurred in the user's activity. Further, the relay terminal device 300 detects an abnormality that has occurred in the user's activity, and then transmits a signal for instructing the imaging terminal device 500 to start capturing an image of the user and record the imaging data.

The relay terminal device 300 is obtained by a smartphone, a tablet, a notebook personal computer, a gateway, or the like.

The reception unit 301 receives the information on the user's activity from the sensor terminal device 200 via the communication network NW. The reception unit 301 corresponds to the transmission and reception unit 15 (FIG. 1).

The storage unit 302 stores the history of the information on the user's activity received by the reception unit 301, the abnormality that occurred in the user's activity detected by the data analysis unit 303, and the information on the user's activity acquired by the sensor terminal device 200. The storage unit 302 corresponds to the storage unit 14 (FIG. 1).

The data analysis unit 303 analyzes the information on the user's activity received by the reception unit 301, and detects an abnormality that has occurred in the user's activity. The data analysis unit 303 corresponds to the data analysis unit 11 including the body motion calculation unit 110 and the determination unit 111 described in FIGS. 1 and 2.

When the data analysis unit 303 detects the occurrence of an abnormality in the user's activity, the imaging control unit 304 generates a signal for instructing the imaging terminal device 500 to start capturing an image of the user and record the imaging data.

The transmission unit 305 transmits the signal generated by the imaging control unit 304 to instruct the imaging terminal device 500 to start capturing an image and recording the imaging data to the imaging terminal device 500 via the communication network NW. The transmission unit 305 corresponds to the transmission and reception unit 15 (FIG. 1).

Functional Block of External Terminal Device

The external terminal device 400 includes a reception unit 401, an imaging data acquisition unit 402, a storage unit 403, and a transmission unit 404. The external terminal device 400 receives the imaging data that is obtained by the imaging terminal device 500 capturing an image of the user in accordance with the reception of an instruction from the relay terminal device 300 via the communication network NW, and stores the received imaging data in the storage unit 403.

The external terminal device 400 is obtained by a smartphone, a tablet, a notebook personal computer, a gateway, or the like similarly to the relay terminal device 300. The external terminal device 400 includes the storage unit 403 that stores the received imaging data.

The reception unit 401 receives the imaging data from the imaging terminal device 500 via the communication network NW. In addition, the reception unit 401 receives a signal indicating that the user's fall has been detected from the relay terminal device 300 via the communication network NW. The reception unit 401 corresponds to the transmission and reception unit 15 (FIG. 1).

The imaging data acquisition unit 402 acquires the imaging data captured and recorded by the imaging terminal device 500. For example, in a case where the signal indicating that the user's fall has been detected is received from the relay terminal device 300, the imaging data acquisition unit 402 can be configured to request the imaging terminal device 500 to acquire the imaging data after the elapse of a predetermined time and acquire the recorded imaging data.

The storage unit 403 stores the imaging data acquired from the imaging terminal device 500. The storage unit 403 corresponds to the storage unit 14 (FIG. 1).

The transmission unit 404 can transmit the imaging data stored in the storage unit 403 to an external terminal device (not illustrated) or the like. The transmission unit 404 corresponds to the transmission and reception unit 15 described in FIG. 1.

Functional Block of Imaging Terminal Device

The imaging terminal device 500 includes a reception unit 501, an imaging unit 502, a storage unit 503, and a transmission unit 504. When an instruction to start image capturing from the relay terminal device 300 is received, the imaging terminal device 500 starts capturing an image of the user and recording the imaging data in the storage unit 503.

The reception unit 501 receives an instruction signal to start capturing an image of the user and recording the imaging data from the relay terminal device 300 via the communication network NW.

The imaging unit 502 corresponds to the camera 100 (FIGS. 1 and 4) that captures an image of the user. The imaging unit 502 performs image capturing, for example, until a set time of a timer (not illustrated) has elapsed since the instruction signal to start image capturing from the relay terminal device 300 has been received. Alternatively, image capturing can be ended by receiving an instruction signal to stop image capturing from the relay terminal device 300.

The storage unit 503 records the imaging data captured by the imaging unit 502.

The transmission unit 504 transmits the imaging data recorded in the storage unit 503 to the external terminal device 400 via the communication network NW.

Operating Sequence of Monitoring System

Figure 9:
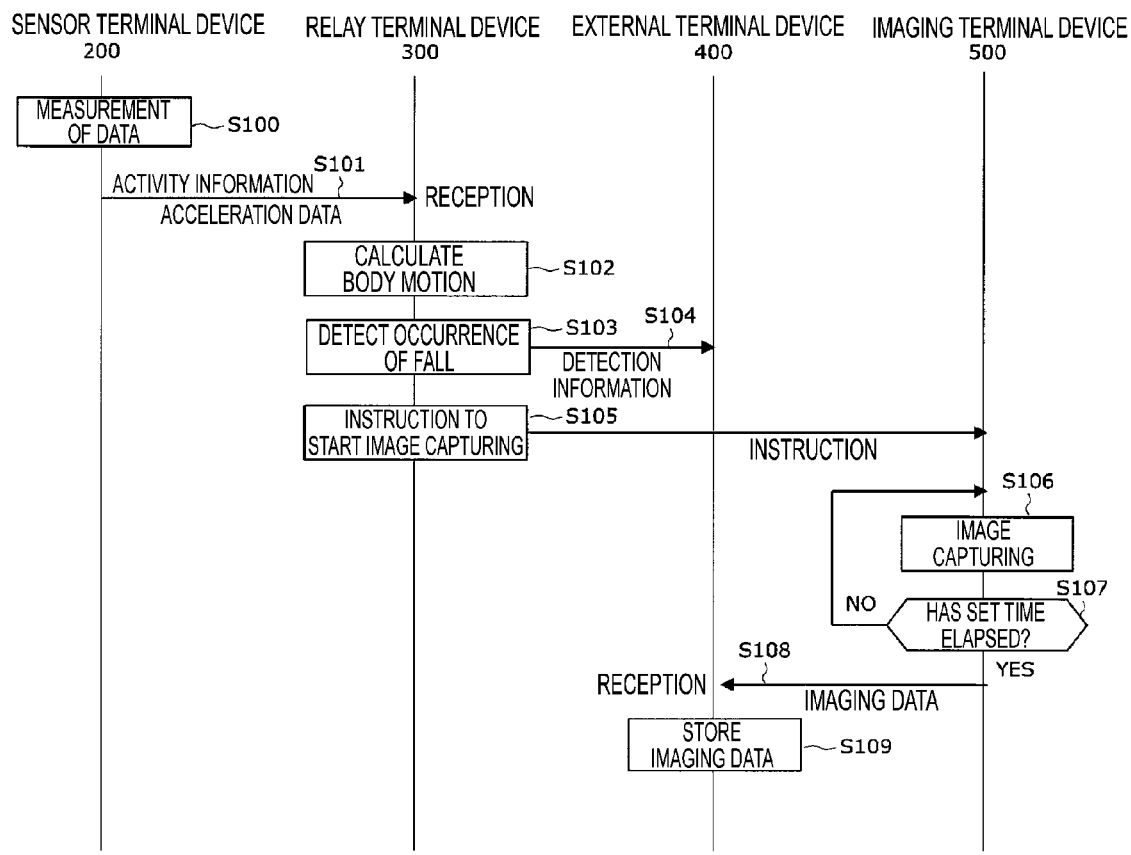
FIG. 9 is a sequence diagram illustrating operations of the monitoring system according to the first embodiment.

Next, an operating sequence of the monitoring system having the specific configuration described in FIGS. 6 to 8 will be described with reference to the sequence diagram of FIG. 9.

First, the sensor terminal device 200 is, for example, worn by the user to measure the user's 3-axis acceleration as the information on the user's activity (step S100). The sensor terminal device 200 obtains a digital signal of the measured acceleration, and performs noise removal as necessary.

Next, the sensor terminal device 200 transmits acceleration data as the activity information to the relay terminal device 300 via the communication network NW (step S101). When the acceleration data is received from the sensor terminal device 200, the relay terminal device 300 calculates the user's body motion from the acceleration data (step S102). Next, in a case where the calculated value of the body motion satisfies the setting criterion, the relay terminal device 300 detects the occurrence of the user's fall (step S103). More specifically, in a case where the norm of 3-axis acceleration is calculated as the body motion and the calculated value of the body motion exceeds, for example, 2 [G], the data analysis unit 303 of the relay terminal device 300 determines that the user has fallen off the bed or the like.

In addition, when the occurrence of a fall is detected in step S103, the relay terminal device 300 can transmit a detection signal to the external terminal device 400 (step S104).

Next, the imaging control unit 304 of the relay terminal device 300 transmits a signal for instructing the imaging terminal device 500 to start capturing an image of the user and recording the imaging data (step S105). Thereafter, the imaging terminal device 500 starts capturing an image of the user and recording the imaging data (step S106). Thereafter, for example, when a set time of a timer or the like elapses (step S107), the recorded imaging data is transmitted to the external terminal device 400 (step S108).

Alternatively, the external terminal device 400 may be configured to request the imaging data from the imaging terminal device 500 after a certain period of time has elapsed since the detection signal was received in step S104, and acquire the imaging data from the imaging terminal device 500. In addition, when the imaging data is transmitted to the external terminal device 400, the imaging terminal device 500 may be configured to erase the data in the memory (the storage unit 503).

Thereafter, the external terminal device 400 stores the received imaging data in the storage unit 403 (step S109).

As described above, according to the first embodiment, the information on the user's activity is acquired, the acquired activity information is analyzed, the occurrence of an abnormality in the user's activity is detected, and the camera 100 is instructed to capture an image of the user and record the imaging data after the detection of the abnormality. Because the camera 100 performs image capturing and recording only during a period when an abnormality has occurred in the user's activity, it is possible to perform monitoring with a reduced burden on the user.

In addition, according to the first embodiment, because a time during which the camera 100 records the imaging data is limited, it is possible to reduce the amount of the imaging data.

In addition, according to the first embodiment, the imaging data includes only a state in which an abnormality has occurred in the user's activity including a fall or the like. Thus, for example, by reproducing imaging data having a short recording time, medical or nursing care staff in charge of treatment or nursing care of the user can immediately ascertain whether the user has hit his or her head along with a fall.

Second Embodiment

Next, a second embodiment of the present disclosure will be described. Meanwhile, in the following description, the same components as those in the above-described first embodiment are denoted by the same reference numerals and signs, and the description thereof will be omitted.

In the first embodiment, a case has been described in which the data analysis unit 11 calculates the body motion from the information on the user's activity acquired by the sensor data acquisition unit 10, and the camera 100 is caused to start capturing an image and recording the imaging data at a point in time when the occurrence of the user's fall is detected in a case where the value of the body motion satisfies the setting criterion. On the other hand, in the second embodiment, a determination unit 111A performs two-step threshold processing, the camera 100 is caused to start image capturing and recording from a point in time when a body motion indicating immediately before the user's fall occurs, and the camera 100 is caused to erase the imaging data that has already been recorded in a case where the user does not fall within a certain period of time.

Figure 10:
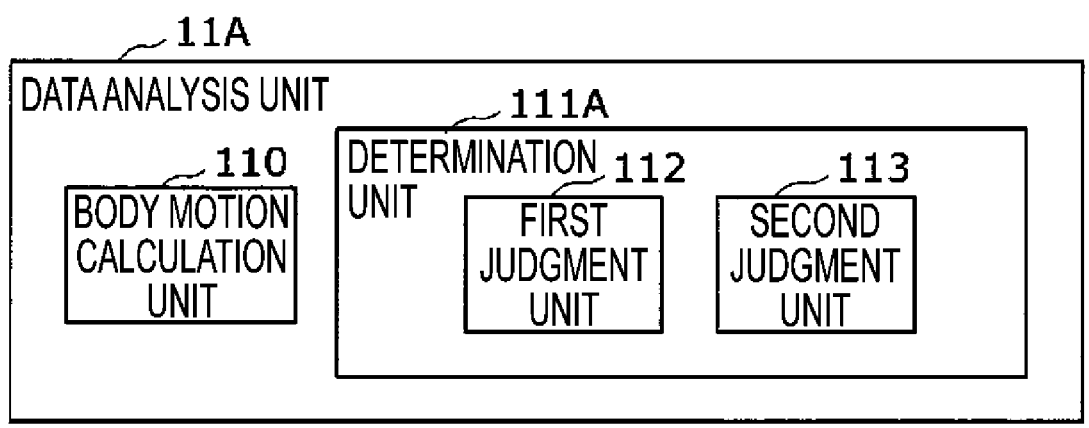
FIG. 10 is a block diagram illustrating a configuration of a data analysis unit according to a second embodiment.
Figure 11:
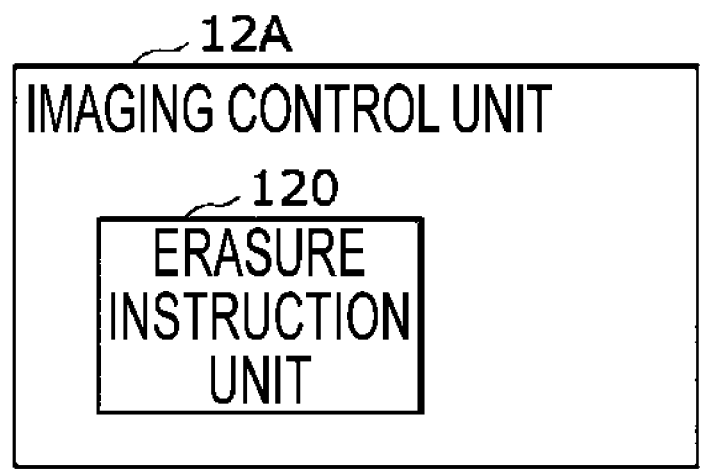
FIG. 11 is a block diagram illustrating a configuration of an imaging control unit according to the second embodiment.

As illustrated in FIG. 10, a data analysis unit 11A included in a monitoring system according to the second embodiment includes a determination unit 111A having a first judgment unit 112 and a second judgment unit 113. In addition, as illustrated in FIG. 11, the imaging control unit 12A includes an erasure instruction unit 140. The monitoring system according to the present embodiment is different from the monitoring system according to the first embodiment in the configuration of the data analysis unit 11A and the imaging control unit 12A. Hereinafter, a description will be given with focus on components different from those of the first embodiment.

Functional Block of Data Analysis Unit

As illustrated in FIG. 10, the data analysis unit 11A includes the body motion calculation unit no and the determination unit 111A. The determination unit 111A includes the first judgment unit 112 and the second judgment unit 113.

The body motion calculation unit no calculates the user's body motion from the user's acceleration data acquired by the sensor data acquisition unit 10. The body motion calculation unit no can calculate the norm of 3-axis acceleration as the body motion.

Next, the first judgment unit 112 and the second judgment unit 113 included in the determination unit 111A will be described. As illustrated in FIG. 3, immediately before the sleeping subject falls off the bed ("b" in FIG. 3), the subject is performing a rising operation ("c" in FIG. 3). Because the value of the body motion fluctuates at the time of rising immediately before the subject falls, the value of the body motion corresponding to the rising operation can be set as a first threshold. Specifically, 1.05 [G] slightly higher than 1 [G] which is the body motion in a sleeping state is set as the first threshold.

In addition, as a second threshold, the value of the body motion equivalent to a fall, for example, 4 [G] or the like, is set in order to detect a body motion indicating falling off the bed in "b" of FIG. 3.

The determination unit 111A performs two-step threshold processing based on the first threshold and the second threshold.

The first judgment unit 112 judges whether the value of the user's body motion calculated by the body motion calculation unit no exceeds the first threshold.

In a case where the first judgment unit 112 judges that the value of the user's body motion exceeds the first threshold, the second judgment unit 113 judges whether the value of the body motion further exceeds the second threshold before a set period elapses. For example, as illustrated in FIG. 3, in a case where it is detected whether the sleeping user has fallen off the bed, it is judged whether the value of the body motion exceeds the second threshold before, for example, 5 minutes elapses from a point in time when the value exceeded the first threshold. The length of the set period can be set in accordance with the size of the body motion caused by the user's specific activity desired to be detected and an activity related to the activity such as the rising operation immediately before a fall, and the time interval of occurrence.

Functional Block of Imaging Control Unit

As illustrated in FIG. 11, the imaging control unit 12A includes an erasure instruction unit 120.

In a case where the first judgment unit 112 judges that the value of the user's body motion exceeds the first threshold, the imaging control unit 12A instructs the camera 100 to start capturing an image of the user and recording the imaging data.

In a case where the second judgment unit 113 judges that the value of the user's body motion exceeds the first threshold and then does not exceed the second threshold within the set period, the erasure instruction unit 120 instructs the camera 100 to erase the imaging data that has already been recorded.

Functional Block of Imaging Terminal Device

Figure 12:
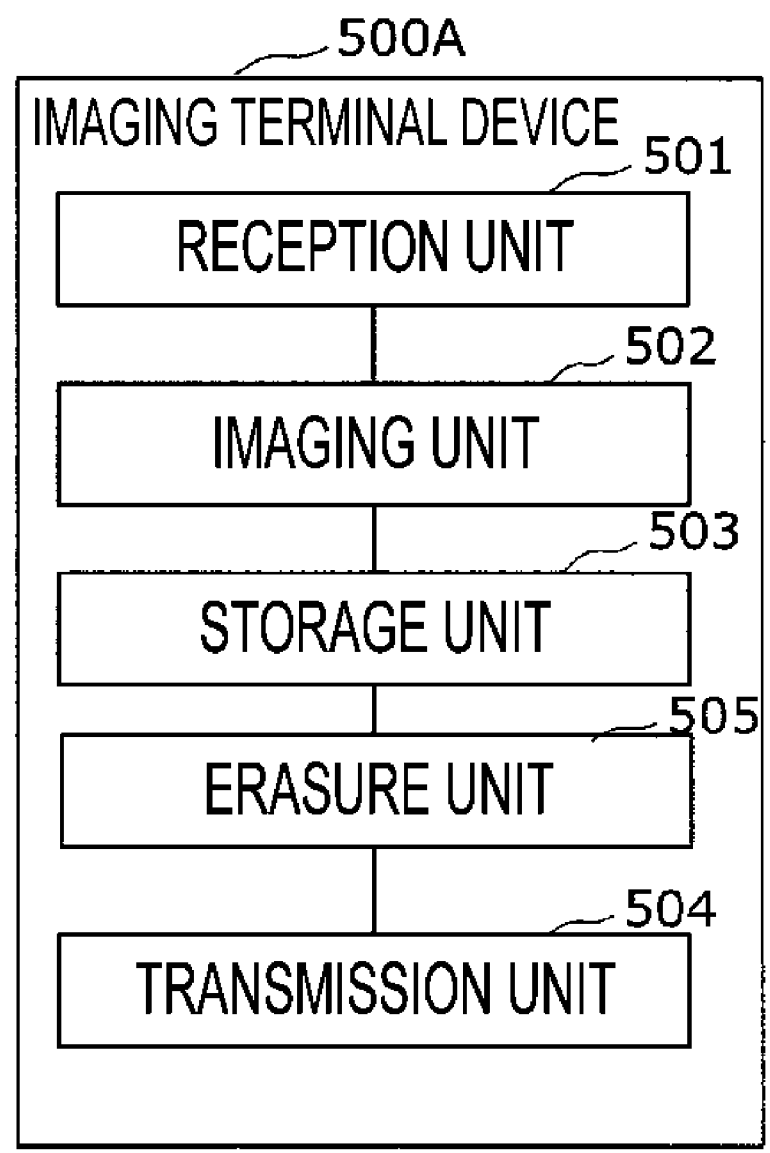
FIG. 12 is a block diagram illustrating a configuration of an imaging terminal device according to the second embodiment.

FIG. 12 is a block diagram illustrating a configuration of an imaging terminal device 500A according to the present embodiment in the specific configuration example (FIG. 8) of the monitoring system.

The imaging terminal device 500A includes a reception unit 501, an imaging unit 502, a storage unit 503, an erasure unit 505, and a transmission unit 504. Components other than the erasure unit 505 are the same as the components of the imaging terminal device 500 (FIG. 8) described in the first embodiment.

When an instruction signal to erase the imaging data recorded in the storage unit 503 is received from the relay terminal device 300, the erasure unit 505 erases the imaging data recorded in the storage unit 503.

Monitoring Method

Figure 13:
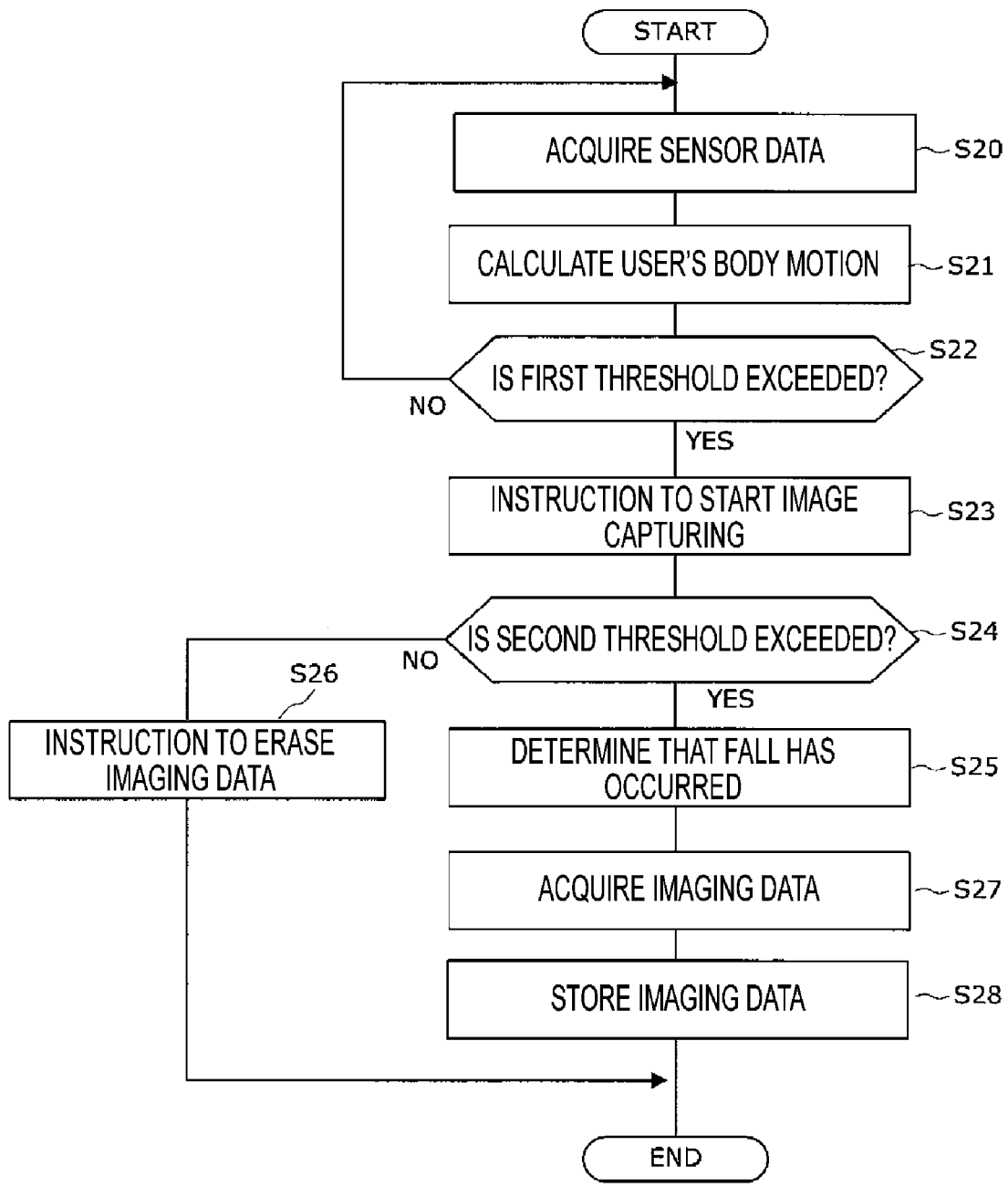
FIG. 13 is a flowchart illustrating a monitoring method according to the second embodiment.

Next, operations of the monitoring system according to the present embodiment having the above-described configuration will be described with reference to the flowchart of FIG. 13. First, the camera 100 is installed in advance in a hospital room where the user sleeps, a rehabilitation room where the user undergoes rehabilitation, or the like. In addition, when the sensor 105 including a 3-axis acceleration sensor is worn by the user and the measurement of the user's acceleration is started as activity information, the following processes are executed.

First, the sensor data acquisition unit 10 acquires the user's acceleration signal measured by the sensor 105 (step S20). In step S1, the sensor data acquisition unit 10 performs known signal processing such as amplification, AD conversion, or noise removal on the acquired acceleration signal which is the information on the user's activity. The acquired acceleration data of the user is stored in the storage unit 14.

Next, the body motion calculation unit no calculates the user's body motion from the user's acceleration data acquired in step S20 (step S21).

Next, in a case where the first judgment unit 112 judges that the value of the user's body motion calculated in step S21 exceeds the first threshold (step S22: YES), the imaging control unit 12A instructs the camera 100 to start capturing an image of the user and recording the imaging data (step S23). The processes of steps S20 and S21 are repeated until the value of the user's body motion exceeds the first threshold in step S22 (step S22: NO).

Next, in a case where the second judgment unit 113 judges that the value of the user's body motion exceeds the second threshold within the set period (for example, 5 minutes or the like) from a point in time when the value of the user's body motion exceeds the first threshold (step S24: YES), the determination unit 111A determines that the user has fallen (step S25). Thereafter, the imaging data acquisition unit 13 acquires the imaging data from the camera 100 (step S27). Next, the storage unit 14 stores the acquired imaging data (step S28).

On the other hand, in a case where the value of the user's body motion does not exceed the second threshold within the set period in step S24 (step S24: NO), the erasure instruction unit 120 instructs the camera 100 to erase the imaging data that has already been recorded (step S26).

As described above, according to the second embodiment, the camera 100 starts capturing an image of the user and recording the imaging data at a point in time when the occurrence of the rising operation immediately before the user's fall is detected through the two-step threshold processing. Thus, the state of the user falling is included in the imaging data more reliably, and thus it is possible to perform monitoring the user more reliably.

In addition, according to the second embodiment, in a case where the body motion indicating a fall does not occur within the set period even when the body motion that may be a sign of the user's fall is detected, the imaging data recorded in the camera 100 is erased, and thus it is possible to perform monitoring with a reduced burden on the user.

Third Embodiment

Next, a third embodiment of the present disclosure will be described. Meanwhile, in the following description, the same components as those in the above-described first and second embodiments are denoted by the same reference numerals and signs, and the description thereof will be omitted.

In the first and second embodiments, a case where the body motion calculation unit 110 calculates the norm of 3-axis acceleration as the user's body motion has been described. In contrast, in the third embodiment, the body motion calculation unit no obtains a value indicating the body motion by calculating values obtained by filtering the norm of the acceleration value, and the average, standard deviation, variance, or RMS of the values obtained by filtering the norm of the acceleration value in a certain period.

The values obtained by filtering the norm of the acceleration value by the body motion calculation unit no or a further averaged value is used as the body motion, and thus the value is smoothed through filtering or average processing. This makes it easy for the determination unit 111 according to the first embodiment or the first judgment unit 112 and the second judgment unit 113 according to the second embodiment to perform the threshold processing. In addition, because the variance, standard deviation, or RMS takes a positive value, the threshold processing is also made easy in this case, and thus it is possible to more easily detect the occurrence of an abnormality in the user's activity.

Fourth Embodiment

Next, a fourth embodiment of the present disclosure will be described. Meanwhile, in the following description, the same components as those in the above-described first to third embodiments are denoted by the same reference numerals and signs, and the description thereof will be omitted.

In the first to third embodiments, a case where the body motion is calculated from the user's acceleration measured as the information on the user's activity has been described. In contrast, in the fourth embodiment, in a case where the user's posture is calculated from the user's acceleration instead of the body motion and a change in the calculated posture of the user has a predetermined change pattern, a data analysis unit 11B determines that an abnormality has occurred in the user's activity.

Functional Block of Data Analysis Unit

Figure 14:
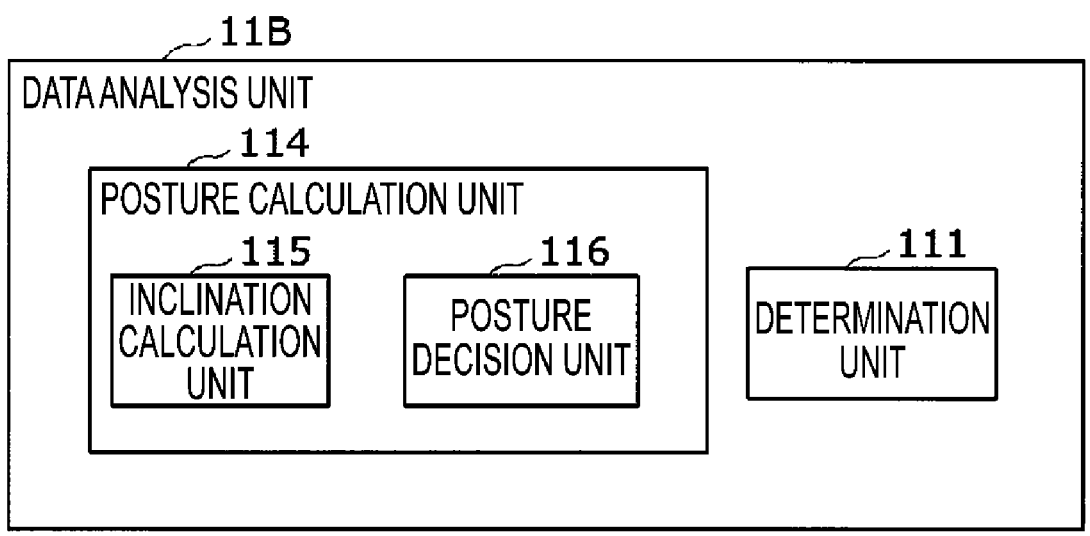
FIG. 14 is a block diagram illustrating a configuration of a data analysis unit according to a fourth embodiment.

FIG. 14 is a functional block diagram of the data analysis unit 11B according to the present embodiment. As illustrated in FIG. 14, the data analysis unit 11B includes a posture calculation unit 114 and the determination unit (second determination unit) 111. Components other than the data analysis unit 11B are the same as those of the first to third embodiments, and will be described below with reference to components (FIG. 1) described in the first embodiment.

The posture calculation unit 114 calculates the user's posture from the acceleration which is the information on the user's activity acquired by the sensor data acquisition unit 10. The posture calculation unit 114 includes an inclination calculation unit 115 and a posture decision unit 116.

The inclination calculation unit 115 obtains the angle of inclination of the user's upper body from the user's acceleration. For example, as disclosed in PTL 1, the inclination calculation unit 115 calculates the inclinations θ and φ [degree] of the sensor 105 to the gravitational acceleration of the acceleration. Here, θ (−90≤θ<270) is the inclination of the Z axis of the sensor 105 in the vertical direction, and φ (−90≤φ<270) is the inclination of the X axis of the sensor 105 in the vertical direction.

[Math. 1]

$$\theta = \frac{180}{\pi}\cos^{-1}\left(\frac{A_z}{\sqrt{A_x^2 + A_y^2 + A_z^2}}\right) + 90 \ldots \text{ (when } A_y \geq 0) \quad (1)$$

$$\theta = -\frac{180}{\pi}\cos^{-1}\left(\frac{A_z}{\sqrt{A_x^2 + A_y^2 + A_z^2}}\right) + 90 \ldots \text{ (when } A_y < 0)$$

$$\phi = \frac{180}{\pi}\cos^{-1}\left(\frac{A_x}{\sqrt{A_x^2 + A_y^2 + A_z^2}}\right) + 90 \ldots \text{ (when } A_y \geq 0) \quad (2)$$

$$\phi = -\frac{180}{\pi}\cos^{-1}\left(\frac{A_x}{\sqrt{A_x^2 + A_y^2 + A_z^2}}\right) + 90 \ldots \text{ (when } A_y < 0)$$

Ax, Ay, and Az are accelerations in the X, Y, and Z-axis directions measured by the sensor 105, respectively, and the unit is gravitational acceleration G (1.0 G≈9.8 m/s2). In Equations (1) and (2), by obtaining the ratio of the uniaxial measured value to the norm which is the magnitude of a composite vector of the accelerations in the X, Y, and Z-axis directions measured by the sensor 105 and further obtaining the inverse function of cosine, the inclination of the sensor 105 (the sensor terminal device 200 of FIG. 8) is calculated as a value having an angle dimension.

The posture decision unit 116 decides the user's posture from the inclination of the sensor 105 obtained by the inclination calculation unit 115. For example, the posture decision unit 116 decides the posture by comparing the values of θ and φ calculated in Equations (1) and (2) with the threshold. The inclination of the sensor 105 reflects the inclination of the upper body of the user wearing the sensor terminal device 200 provided with the sensor 105.

The posture decision unit 116 can decide the user's posture by sorting cases by the range or the values of θ and φ disclosed in PTL 1. Specifically, for the user's posture, the values of θ and φ are classified into six kinds, that is, upright, inverted, supine, prone, left side-body up, and right side-body up. For example, the posture decision unit 116 decides that the user is in a supine posture when [130≤φ≤230] and [−40≤θ<30] are satisfied or when [130≤φ≤230] and [140<θ<220] are satisfied.

In addition, the posture decision unit 116 decides that the user's posture is upright when [30≤θ<140] is satisfied.

Alternatively, the posture decision unit 116 can also decide the user's posture by classifying the values of θ and φ into two kinds, that is, a waking-up state and a lying-down state.

Figure 15:
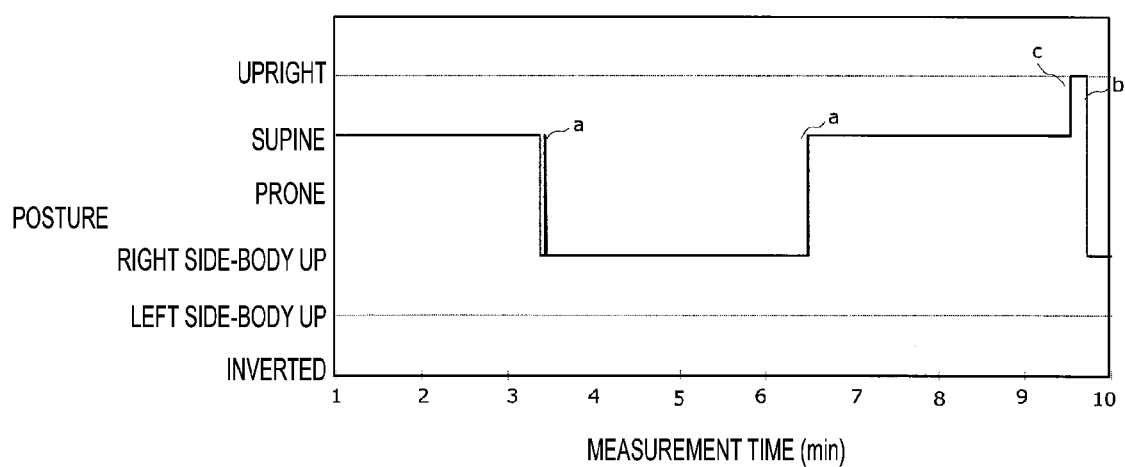
FIG. 15 is a diagram illustrating the data analysis unit according to the fourth embodiment.

FIG. 15 is a diagram illustrating the posture of a sleeping subject corresponding to FIG. 3 in a case where the user's posture is classified into six kinds. In FIG. 15, "a" indicates a change in posture when the subject rolls over. In addition, "b" indicates a change in posture when the subject falls off the bed, and "c" indicates a change in rise posture immediately before a fall.

As illustrated in FIG. 15, when the subject performs a rising operation ("c" in FIG. 15), the posture transitions from supine to upright. On the other hand, when rolling over ("a" in FIG. 15), the posture transitions from supine to prone or from prone to supine. From this, the pattern of a change in posture makes it possible to distinguish between rolling over and rising.

In a case where a change in the user's posture decided by the posture decision unit 116 is a set change pattern, the determination unit 111 determines that an abnormality has occurred in the user's activity. As described in FIG. 15, in a case where the user's posture changes from supine indicating rise to upright, which is likely to occur immediately before a fall, the determination unit 111 determines that a rise which is an abnormality of the user's activity has occurred.

When an abnormality that has occurred in the user's activity is detected by the data analysis unit 11B, the imaging control unit 12 instructs the camera 100 to capture an image of the user and record the imaging data. Meanwhile, as described above, after a preset period has elapsed since the start of user image capturing and recording, the camera 100 can be configured to stop image capturing and recording.

Monitoring Method

Figure 16:
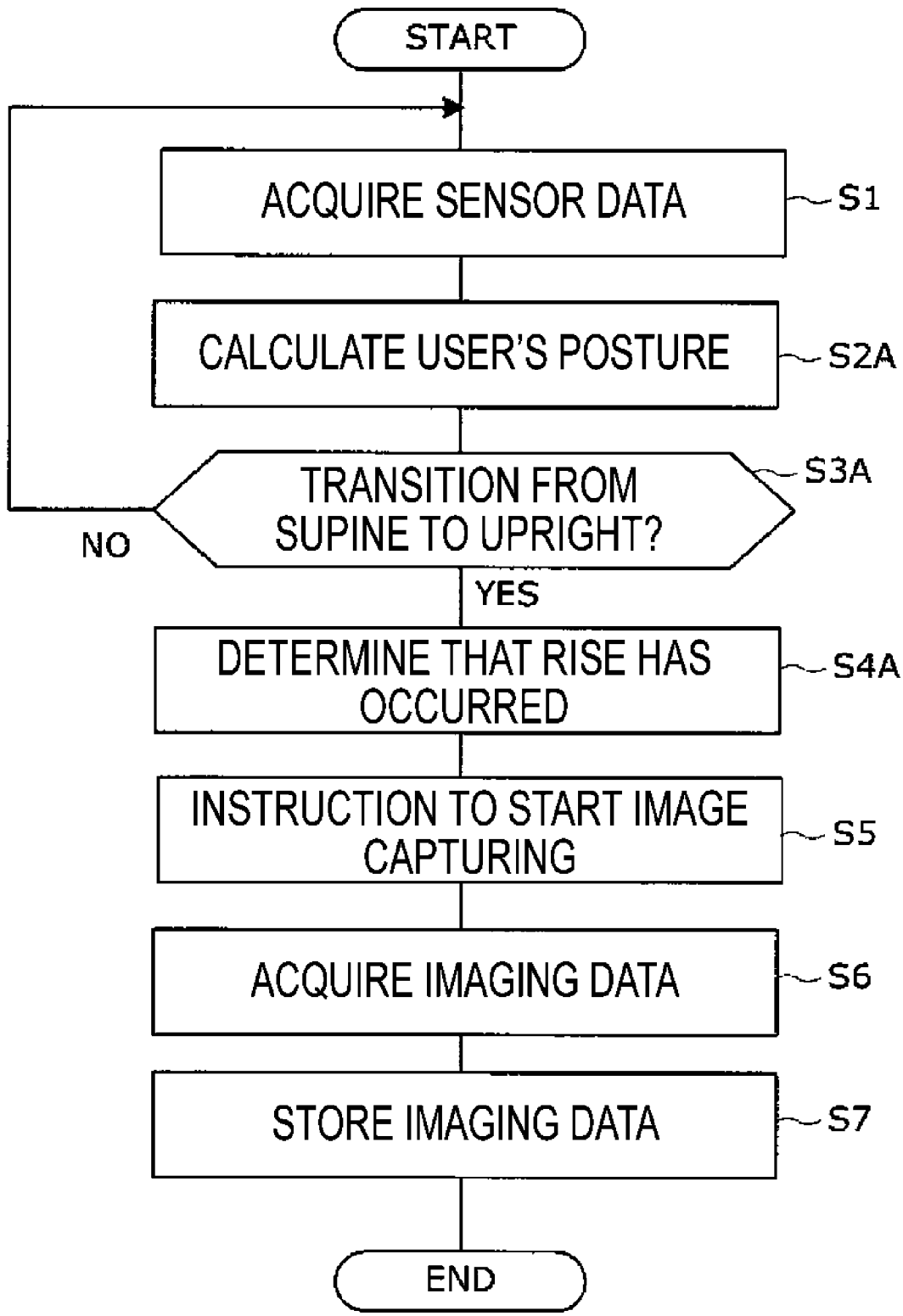
FIG. 16 is a flowchart illustrating a monitoring method according to the fourth embodiment.

Next, operations of the monitoring system according to the present embodiment having the above-described configuration will be described with reference to the flowchart of FIG. 16. First, the camera 100 is installed in advance in a room or the like where the user performs activities such as sleeping or rehabilitation. In addition, when the sensor 105 including a 3-axis acceleration sensor is mounted on the user in advance and the measurement of an acceleration is started as the activity information, the following processes are executed.

First, the sensor data acquisition unit 10 acquires the user's acceleration signal measured by the sensor 105 (step S1). In step S1, the sensor data acquisition unit 10 performs known signal processing such as amplification, AD conversion, or noise removal on the acquired acceleration signal which is the information on the user's activity. The acquired time-series of the user's acceleration data is stored in the storage unit 14.

Next, the posture calculation unit 114 calculates the user's posture from the user's acceleration data acquired in step S1 (step S2A).

Next, in a case where the user's posture calculated in step S2A transitions from supine to upright (step S3A: YES), the determination unit 111 determines that an abnormality has occurred in the user's activity, that is, a rise immediately before the user's fall has occurred (step S4A).

Next, when the determination unit 111 determines that a rise immediately before the user's fall has occurred, the imaging control unit 12 instructs the external camera 100 to start capturing an image of the user and record the imaging data (step S5). Thereafter, the camera 100 starts capturing an image of the user, captures images of states before the user hits the floor or the like from immediately before a fall, and records the imaging data in a memory.

Next, the imaging data acquisition unit 13 acquires the imaging data recorded by the camera 100 (step S6). Thereafter, the acquired imaging data is stored in the storage unit 14 (step S7). Meanwhile, the transmission and reception unit 15 can send out the imaging data stored in the storage unit 14 to an external terminal device or the like.

As described above, according to the fourth embodiment, the data analysis unit 11B calculates the user's posture from the user's acceleration data, determines that an abnormality has occurred in the user's activity in a case where a change in the user's posture has a predetermined pattern of a change in posture, and instructs the camera 100 to capture an image of the user and record the imaging data. Thus, it is possible to suppress erroneous detection of the posture pattern in a case where the user rolls over, more accurately detect an abnormality that has occurred in the user's activity including the user's fall, and obtain imaging data during that period.

In addition, according to the fourth embodiment, it is possible to more accurately detect the occurrence of an abnormality including the user's fall, and to suppress the occurrence of unnecessary image capturing in the camera 100.

Meanwhile, in the described embodiment, a case where the user's posture described in FIG. 15 is classified into six kinds has been described, but in a case where the user's posture is divided into two kinds, that is, a lying-down state and a waking-up state to decide the user's posture, the posture calculation unit 114 determines that an abnormality has occurred when the user's posture transitions from the lying-down state to the waking-up state, and can instruct the camera 100 to start image capturing.

Fifth Embodiment

Next, a fifth embodiment of the present disclosure will be described. Meanwhile, in the following description, the same components as those in the above-described first to fourth embodiments are denoted by the same reference numerals and signs, and the description thereof will be omitted.

In the first to third embodiments, the body motion is calculated from the user's acceleration, and the value of the body motion is used to detect the occurrence of an abnormality in the activity including the user's fall. In addition, in the fourth embodiment, the user's posture is calculated from the user's acceleration, and the occurrence of an abnormality in the user's activity is detected in a case where a change in the calculated posture matches a set change pattern. In contrast, in the fifth embodiment, a data analysis unit 11C calculates the body motion and posture from the user's acceleration, and detects an abnormality that has occurred in the user's activity using the calculated body motion and posture.

Figure 17:
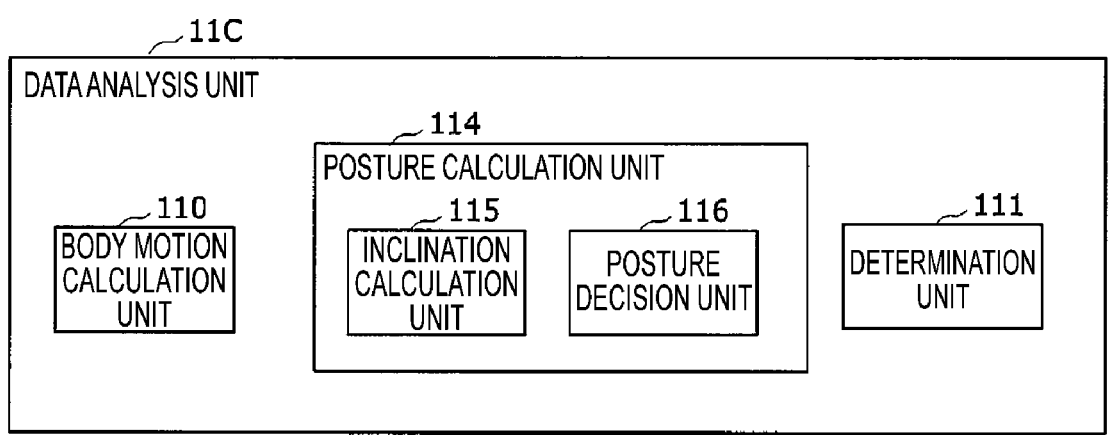
FIG. 17 is a block diagram illustrating a configuration of a data analysis unit according to a fifth embodiment.

FIG. 17 is a block diagram illustrating a configuration of the data analysis unit 11C according to the present embodiment.

The data analysis unit 11C includes the body motion calculation unit 110, the posture calculation unit 114, and the determination unit 111.

The body motion calculation unit 110 calculates the user's body motion from the user's acceleration acquired by the sensor data acquisition unit 10.

The posture calculation unit 114 includes an inclination calculation unit 115 and a posture decision unit 116. The inclination calculation unit 115 uses Equations (1) and (2) described above to obtain the inclination angle of the user's upper body from the user's acceleration.

The posture decision unit 116 decides the user's posture based on the classification of, for example, six kinds of posture disclosed in PTL 1, as illustrated in FIG. 15, from the inclination angle of the user's upper body calculated by the inclination calculation unit 115.

The determination unit 111 determines that an abnormality has occurred in the user's activity in a case where a change in the user's posture calculated by the posture calculation unit 114 has a set change pattern. More specifically, the determination unit 111 determines that a rise has occurred in a case where a change based on the posture calculation unit 114 matches the pattern of a change in posture indicating a rise immediately before the user's fall.

In addition, the determination unit 111 determines that the user's fall has occurred in a case where the value of the user's body motion calculated by the body motion calculation unit no exceeds the value of the body motion indicating the user's fall, for example, the value of the body motion of about 5 [G] as illustrated in FIG. 3.

In a case where the determination unit 111 determines that the user's rise has occurred and the user's fall has occurred from the user's posture, the imaging control unit 12 instructs the camera 100 to start capturing an image of the user and recording the imaging data.

In this way, according to the fifth embodiment, the user's posture and body motion are calculated from the acceleration which is the information on the user's activity, an abnormality that has occurred in the user's activity is detected based on these values, and the camera 100 is instructed to start capturing an image of the user and start recording the imaging data. Thus, particularly, an abnormality occurring in the user's activity such as when the sleeping user falls off the bed can be detected, and an abnormality that has occurred in the user's activity can be detected more accurately by grasping a rise using the user's posture and detecting a fall using the body motion. As a result, it is possible to more reliably capture an image of an abnormality that has occurred in the user's activity such as the state of the user falling off the bed.

Sixth Embodiment

Next, a sixth embodiment of the present disclosure will be described. Meanwhile, in the following description, the same components as those in the above-described first to fifth embodiments are denoted by the same reference numerals and signs, and the description thereof will be omitted.

Figure 18:
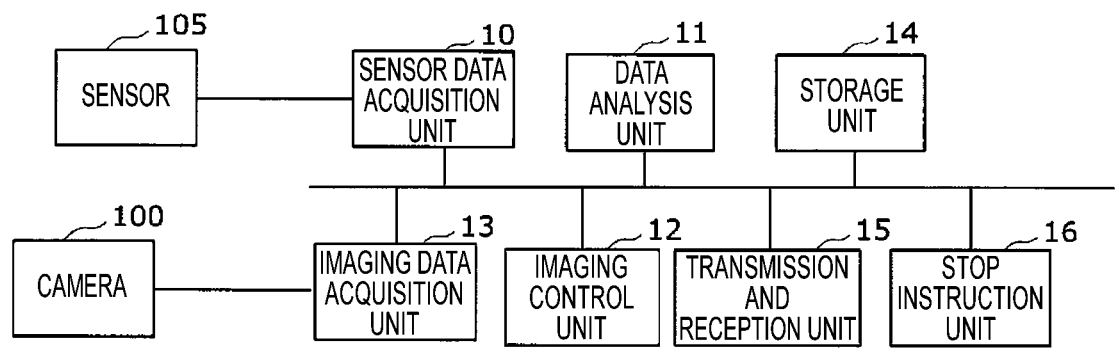
FIG. 18 is a block diagram illustrating a configuration of an imaging control unit according to a sixth embodiment.

As illustrated in FIG. 18, a monitoring system according to the sixth embodiment is different from the configurations according to the first to fifth embodiments in that it further includes a stop instruction unit 16.

Even when the data analysis unit 11 detects an abnormality that has occurred in the user's activity based on the user's acceleration acquired by the sensor data acquisition unit 10, the stop instruction unit 16 sends out an instruction to the imaging data acquisition unit 13 so as not to acquire the imaging data recorded by the camera 100 in a case where the detected time is in a predetermined time slot such as, for example, in the daytime.

The stop instruction unit 16 sends out the stop instruction to the imaging data acquisition unit 13, for example, in a case where a time when the occurrence of an abnormality in the user's activity is detected based on time information acquired from a timepiece or the like included in the monitoring system is in a time slot when it is not necessary to monitor the user's activity such as in the daytime. For example, a case where the user undergoes a rehabilitation exercise with a therapist in the daytime, a time slot when the medical staff is within the reach of the user, or the like can be registered in the storage unit 14 in advance.

Figure 19:
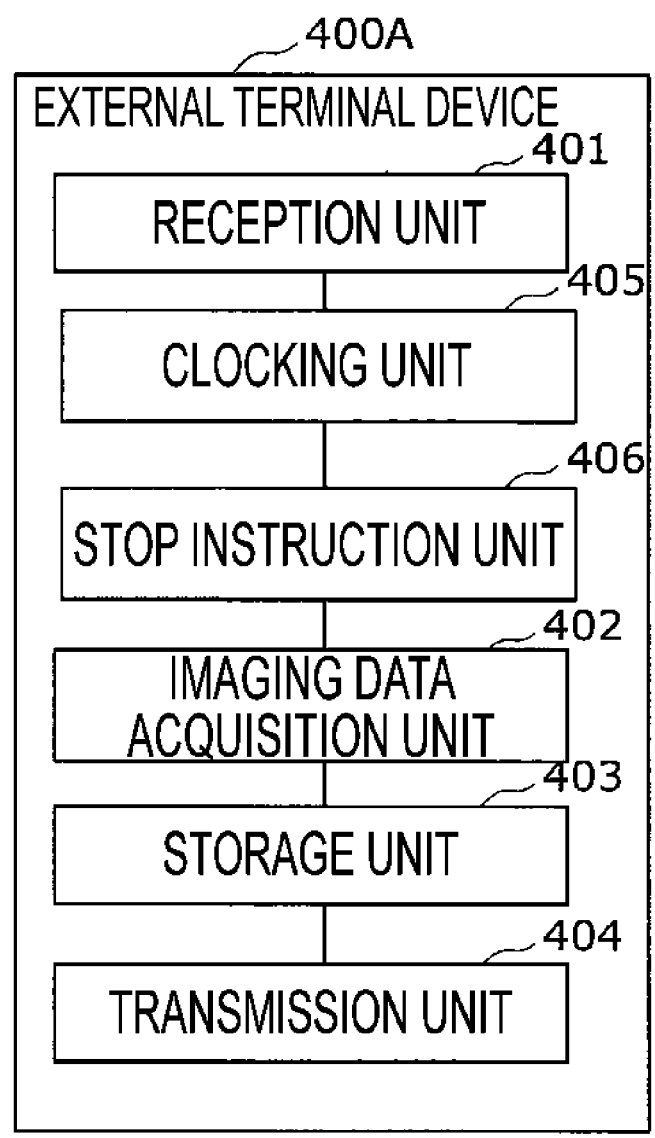
FIG. 19 is a block diagram illustrating a configuration of an external terminal device according to the sixth embodiment.

FIG. 19 is a block diagram illustrating a configuration of an external terminal device 400A included in the specific configuration example (FIG. 8) of the monitoring system.

The external terminal device 400A includes the reception unit 401, a clocking unit 405, a stop instruction unit 406, the imaging data acquisition unit 402, the storage unit 403, and the transmission unit 404.

The clocking unit 405 acquires time information from an internal timepiece, a time server, or the like that clocks a time.

The stop instruction unit 406 prevents the imaging data acquisition unit 402 from acquiring the imaging data captured and recorded by the imaging terminal device 500 in the set time slot based on the time information acquired by the clocking unit 405.

In this manner, even when an abnormality in the user's activity is detected, a case where it is not necessary to monitor the user's activity can be considered when the medical staff or nursing care staff who is in charge of taking care of a user such as a patient are near the user in a time slot such as in the daytime, in a time slot when the user undergoes rehabilitation training, or in a time slot when relatively large body motions such as rising may occur frequently.

The monitoring system according to the sixth embodiment further includes the stop instruction unit 16, and thus is enabled to acquire imaging data only during nighttime hours, for example, from 20:00 to 6:00 am the next day in which it is highly necessary to monitor the presence or absence of the occurrence of an abnormality in the user's activity in reality, and to suppress unnecessary imaging data.

Seventh Embodiment

Next, a seventh embodiment of the present disclosure will be described. Meanwhile, in the following description, the same components as those in the above-described first to sixth embodiments are denoted by the same reference numerals and signs, and the description thereof will be omitted.

Figure 20:
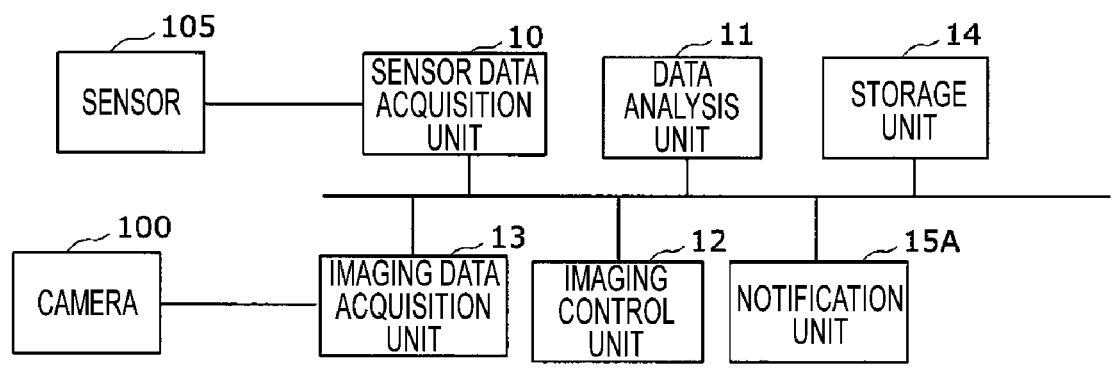
FIG. 20 is a block diagram illustrating a configuration of a monitoring system according to a seventh embodiment.

As illustrated in FIG. 20, a monitoring system according to the seventh embodiment is different from the configurations according to the first to sixth embodiments in that it includes a notification unit 17. FIG. 20 is a block diagram illustrating a configuration of a monitoring system according to the present embodiment.

Figure 21:
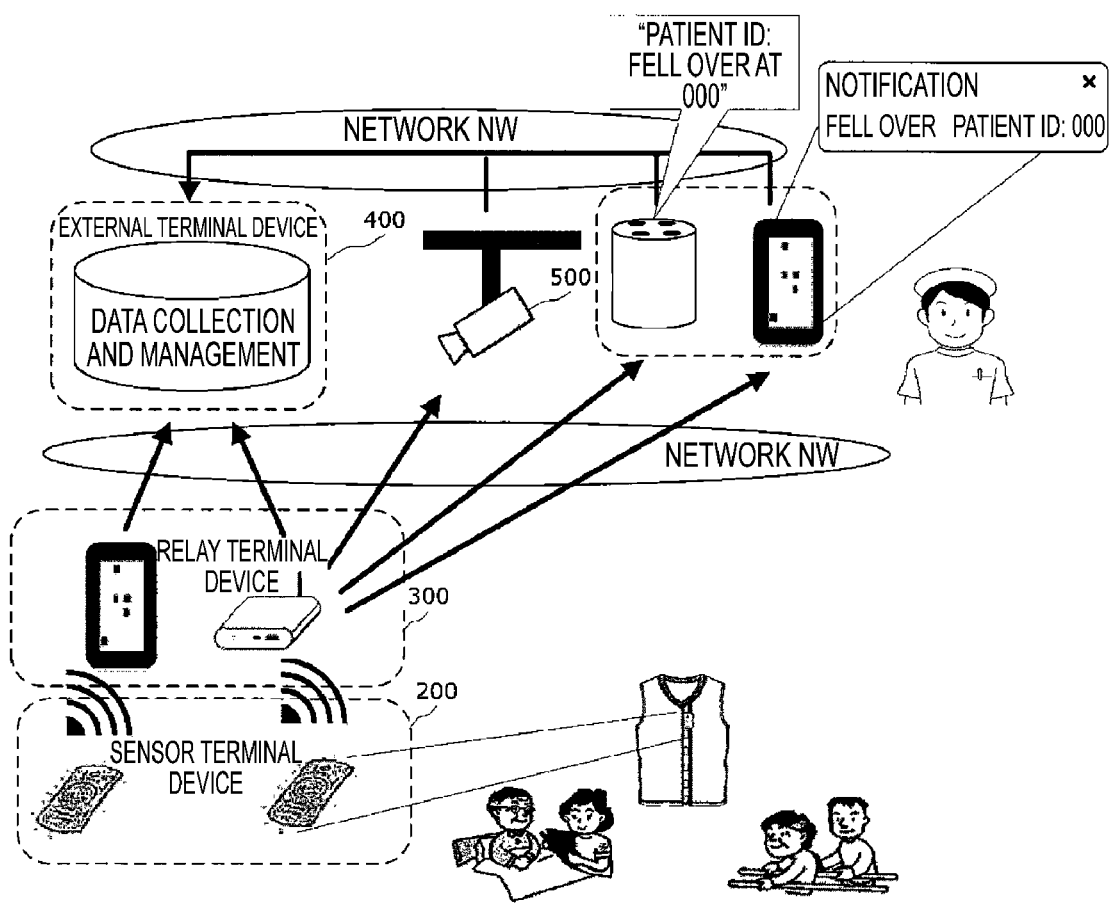
FIG. 21 is a block diagram illustrating an outline of a monitoring system according to the seventh embodiment.

In a case where the occurrence of an abnormality in the user's activity is detected by the data analysis unit 11, the notification unit 17 notifies an external terminal device of the occurrence of an abnormality in the user's activity. For example, as illustrated in FIG. 21, the notification unit 17 can send a notification to a smartphone carried by the medical staff or nursing care staff who is in charge of treatment or nursing care of the user, a smart speaker installed in a room or the like where the medical staff is located, or the like.

In addition, the notification unit 17 can generate notification information and notify an external terminal device of the generated notification information in a case where the data analysis unit 11 detects at least any of the user rising and falling as illustrated in FIG. 3.

In this way, according to the seventh embodiment, in a case where the occurrence of an abnormality in the user's activity is detected, not only the imaging data captured and recorded by the camera 100 is stored in the storage unit 14, but also the external terminal device is notified of the occurrence of an abnormality. Thus, the medical staff or nursing care staff who is in charge of treatment or nursing care of the user can immediately take appropriate measures in response to the occurrence of an abnormality.

Eighth Embodiment

Next, an eighth embodiment of the present disclosure will be described. Meanwhile, in the following description, the same components as those in the above-described first to seventh embodiments are denoted by the same reference numerals and signs, and the description thereof will be omitted.

A case where the monitoring systems according to the first to seventh embodiments instruct the camera 100 to start capturing an image of the user and recording the imaging data when the occurrence of an abnormality in the user's activity is detected has been described. In contrast, in a monitoring system according to the eighth embodiment, the camera 100 constantly captures an image of the user and records the imaging data, and the imaging data recorded by the camera 100 is erased in a case where no abnormality occurs in the user's activity within a certain period of time.

Figure 22:
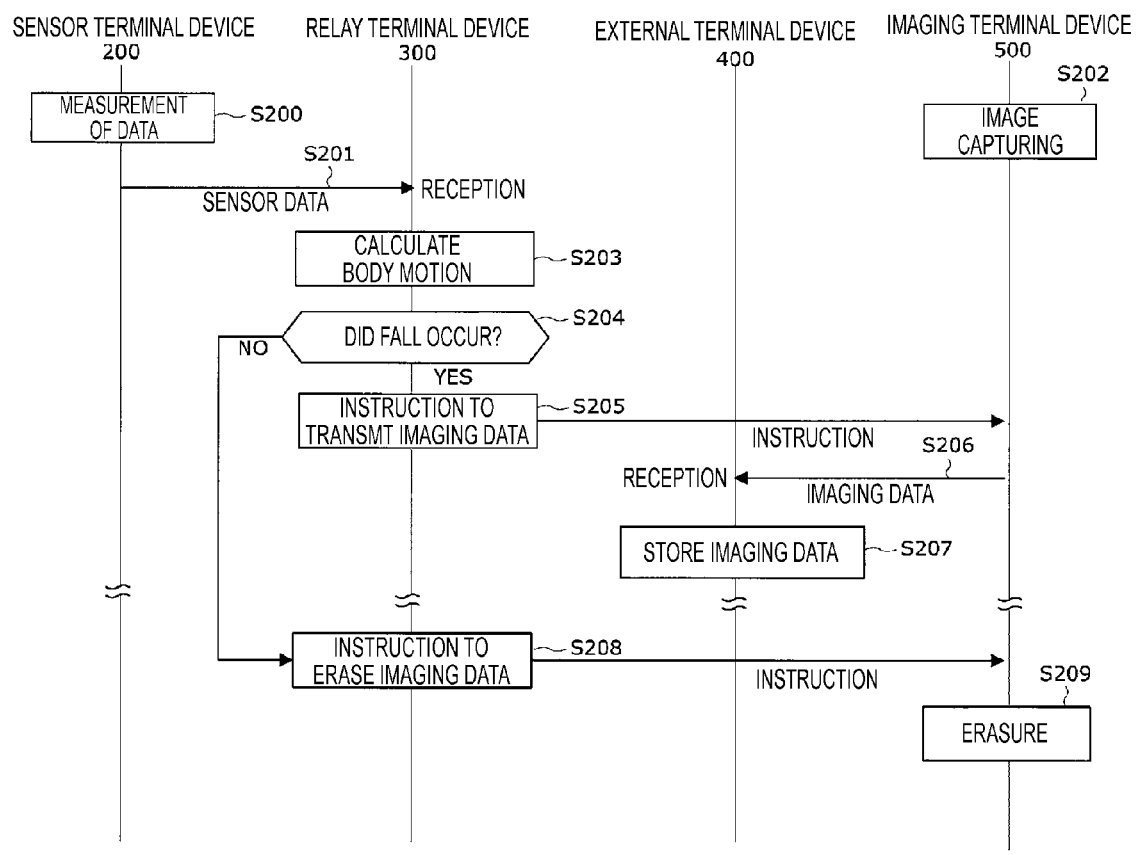
FIG. 22 is a sequence diagram illustrating operations of a monitoring system according to an eighth embodiment.
Figure 23:
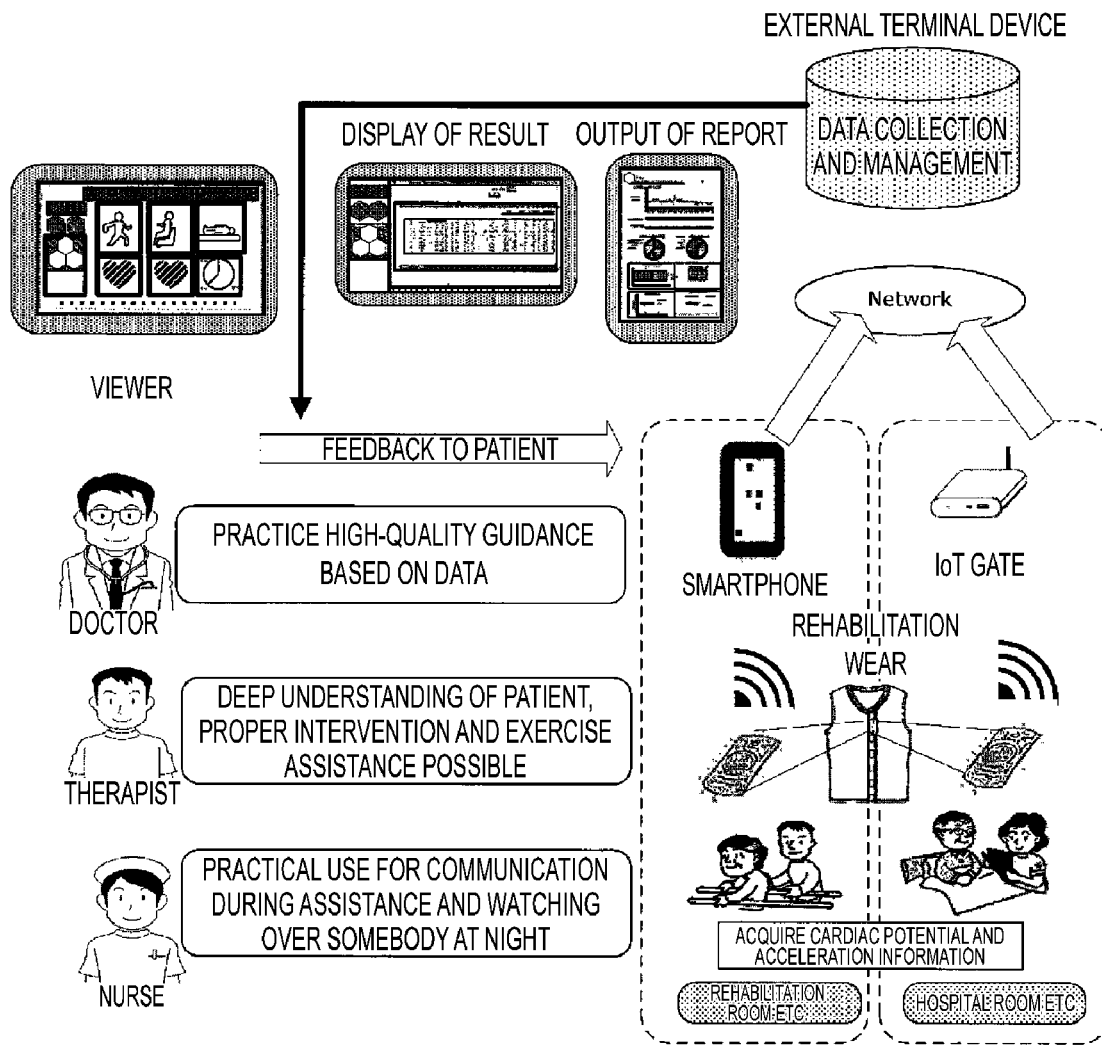
FIG. 23 is a diagram illustrating an outline of a monitoring system of the related art.

FIG. 22 is a sequence diagram illustrating operations of the monitoring system according to the present embodiment. Meanwhile, operations in the specific configuration of the monitoring system described in FIG. 8 will be described below.

First, the sensor terminal device 200 is, for example, worn by the user to measure a 3-axis acceleration as information on the user's activity (step S200). The sensor terminal device 200 obtains a digital signal of the measured acceleration, and performs noise removal as necessary.

On the other hand, the imaging terminal device 500 starts capturing an image of the user and recording the imaging data (step S202).

Next, the sensor terminal device 200 transmits acceleration data as activity information to the relay terminal device 300 via the communication network NW (step S201). When the sensor terminal device 200 receives the acceleration data, the relay terminal device 300 calculates the user's body motion from the acceleration data (step S203). Next, in a case where the value of the calculated body motion satisfies the setting criterion and the occurrence of the user's fall is detected (step S204), the relay terminal device 300 causes the imaging terminal device 500 to transmit the recorded imaging data to the external terminal device 400 (step S205). Meanwhile, the relay terminal device 300 can detect the user's fall based not only on the value of the user's body motion but also on the user's posture.

Thereafter, the imaging terminal device 500 transmits the imaging data that has already been recorded to the external terminal device 400 (step S206). Next, the external terminal device 400 stores the received imaging data in the storage unit 403 (step S207). Meanwhile, the external terminal device 500 can transmit the imaging data to external terminal device (not illustrated) or the like.

On the other hand, in a case where the user's fall is not detected in step S204 by the relay terminal device 300 (step S204: NO), the relay terminal device 300 transmits an instruction to erase the imaging data that has already been recorded to the imaging terminal device 500 (step S208). When receiving the instruction, the imaging terminal device 500 erases the imaging data recorded in the storage unit 503 (step S209). For example, the imaging terminal device 500 can be configured to erase the imaging data captured and recorded for a certain period of time in response to an erasure instruction from the relay terminal device 300.

As described above, according to the eighth embodiment, even when the camera 100 constantly captures an image of the user and records the imaging data, the camera 100 is caused to erase the imaging data that has already been recorded in a case where the data analysis unit 11 does not detect the occurrence of an abnormality in the user's activity. In this way, by leaving the imaging data including the state of the user falling in a memory and erasing the imaging data during a period in which no predetermined change occurs in the user's body motion or posture, it is possible to reliably watch over the user while reducing the user's burden.

Hereinbefore, although the embodiments in the monitoring system, the monitoring method, and the monitoring program of the present disclosure have been described, the present disclosure is not limited to the described embodiments, various modifications that can be conceived by those skilled in the art can be made within the scope of the invention described in the claims.

REFERENCE SIGNS LIST 10, 202 Sensor data acquisition unit
11, 303 Data analysis unit
12, 304 Imaging control unit
13, 402 Imaging data acquisition unit
14, 203, 302, 403, 503 Storage unit
15 Transmission and reception unit
110 Body motion calculation unit
111 Determination unit
101 Bus
102 Processor
103 Main memory
104 Communication I/F
105, 201 Sensor
106 Auxiliary storage device
107 Timepiece
108 Input and output I/O
109 Display device
100 Camera
200 Sensor terminal device
300 Relay terminal device
400 External terminal device
500 Imaging terminal device 204, 305, 404, 504 Transmission unit
301, 401, 501 Reception unit
502 Imaging unit

The invention claimed is:

1. A monitoring system comprising:
a sensor data acquisition device comprising an acceleration sensor, the acceleration sensor configured to acquire an acceleration of a user;
a data analyzer configured to analyze the acceleration of the user and detect occurrence of an abnormality in the acceleration of the user;
an imaging controller configured to instruct an imaging terminal device that captures an image of the acceleration of the user to start capturing an image of the user and record imaging data in a case where the occurrence of the abnormality is detected by the data analyzer;
an imaging data acquisition device configured to acquire the imaging data recorded by the imaging terminal device;
a data storage device configured to store the imaging data acquired by the imaging data acquisition device; and
an output device configured to output the imaging data,
wherein the data analyzer includes:
a posture calculator configured to calculate a posture of the user from the acceleration of the user by calculating a first inclination angle ($\theta$) of a Z-axis of an acceleration sensor worn by the user with respect to a vertical direction and a second inclination angle ($\varphi$) of an X-axis of the acceleration sensor with respect to the vertical direction,
a body motion calculator configured to calculate body motion of the user from the acceleration of the user, and
a first determination device configured to determine that the abnormality has occurred in a case where a value of the body motion of the user satisfies a setting criterion, the first determination device includes:
a first judgment device configured to judge whether the value of the body motion of the user exceeds a first threshold based on the acceleration of the user, wherein the first threshold corresponds to a body motion value associated with a user transitioning from a first posture to a second posture, wherein the first posture is a supine posture and the second posture is an upright posture; the supine posture is determined when either: (a) $130°\leq\varphi\leq230°$ and $-40°\leq\theta<30°$, or (b) $130°\leq\varphi\leq230°$ and $140°<\theta<220°$ and the upright posture is determined when $30°\leq\theta<140°$, and
a second judgment device configured to judge whether the value of the body motion of the user further exceeds a second threshold within a set period in a case where the value of the body motion of the user exceeds the first threshold based on the acceleration of the user, wherein the second threshold corresponds to a body motion value associated with a user falling, and wherein the set period begins when the first judgment device determines that the value of the body motion of the user exceeds the first threshold.

2. The monitoring system according to claim 1, wherein the imaging controller instructs the imaging terminal device to start capturing the image of the user and record the imaging data in a case where the first judgment device judges that the value of the body motion of the user exceeds the first threshold, and the imaging controller instructs the imaging terminal device to erase the imaging data that has already been recorded in a case where the second judgment device judges that the value of the body motion of the user does not exceed the second threshold.

3. The monitoring system according to claim 1, wherein the data analyzer includes a second determination device configured to determine that the abnormality has occurred in a case where a change in the posture of the user matches a set change pattern.

4. The monitoring system of claim 1, wherein the imaging controller is configured to instruct the imaging terminal device that has started capturing an image of the user and recording imaging data in advance to erase the imaging data that has already been recorded in a case where the occurrence of the abnormality is not detected by the data analyzer.

5. The monitoring system of claim 4, wherein the imaging data acquisition device is configured to acquire the imaging data recorded by the imaging terminal device in a case where the occurrence of the abnormality is detected by the data analyzer.

6. The monitoring system according to claim 1, wherein the second judgment device is configured to continuously monitor the value of the body motion of the user during the set period to determine if it exceeds the second threshold.

7. The monitoring system according to claim 1, wherein the body motion is configured to calculate body motion of the user from the acceleration of the user by determining a norm of the acceleration values over a predetermined time period.

8. The monitoring system according to claim 1, wherein the first determination device is further configured to determine that the abnormality has occurred based on a combination of the calculated body motion and the calculated posture of the user.

9. The monitoring system of claim 1, wherein the abnormality is determined to have occurred when the first judgment device detects a rising motion followed by the second judgment device detecting a falling motion within the set period.

10. A monitoring system comprising:
a sensor terminal device configured to output information on an activity of a user which is measured by a sensor worn by the user, the information of the user includes an acceleration of the user;
a relay terminal device configured to receive the information on the activity of the user which is output from the sensor terminal device and output the received information on the activity of the user;
an external terminal device configured to receive the information on the activity of the user which is output from the sensor terminal device or the relay terminal device and cause a storage device to store the received activity information; and
an imaging terminal device configured to start capturing an image of the user in accordance with an instruction, record imaging data, and transmit the imaging data to the external terminal device,
wherein at least any of the sensor terminal device, the relay terminal device, and the external terminal device includes
a sensor data acquisition device configured to acquire the information on the activity of the user,
a data analyzer configured to analyze the acquired information on the activity of the user and detect occurrence of an abnormality in the activity of the user, wherein an abnormality the data analyzer is configured to detect is a change in posture of the user before a fall, wherein the data analyzer includes:
a posture calculator configured to calculate a posture of the user from the acceleration of the user by calculating a first inclination angle (θ) of a Z-axis of an acceleration sensor worn by the user with respect to a vertical direction and a second inclination angle (φ) of an X-axis of the acceleration sensor with respect to the vertical direction,
a body motion calculator configured to calculate body motion of the user from the acceleration of the user,
a fall predictor configured to predict an occurrence of a fall based on a combination of the calculated posture and the calculated body motion of the user, wherein the change in posture before a fall is detected based on the prediction by the fall predictor, and
a first determination device configured to determine whether the calculated posture transitions from a first posture to a second posture, wherein the first posture is a supine posture and the second posture is an upright posture; the supine posture is determined when either: (a) 130°≤φ≤230° and −40°≤θ<30°, or (b) 130°≤φ≤230° and 140°<θ<220° and the upright posture is determined when 30°≤θ<140°,
an imaging controller configured to instruct the imaging terminal device to start capturing an image of the user and record imaging data in a case where the occurrence of the abnormality is detected by the data analyzer, wherein, in response to the detection of a change in posture before a fall, the imaging controller is configured to instruct the imaging terminal device to start capturing an image of the user before the user falls,
an imaging data acquisition device configured to acquire the imaging data recorded by the imaging terminal device,
a data storage device configured to store the imaging data acquired by the imaging data acquisition device, and
an output device configured to output the imaging data.

11. The monitoring system according to claim 10, wherein first determination device is configured to determine that the abnormality has occurred in a case where a value of the body motion of the user satisfies a setting criterion.

12. The monitoring system according to claim 11, wherein the first determination device includes
a first judgment device configured to judge whether the value of the body motion of the user exceeds a first threshold, the first threshold being whether the calculated posture transitions from the first posture to the second posture, and
a second judgment device configured to judge whether the value of the body motion of the user further exceeds a second threshold within a set period in a case where the value of the body motion of the user exceeds the first threshold, the imaging controller instructs the imaging terminal device to start capturing the
image of the user and record the imaging data in a case where the first judgment device judges that the value of the body motion of the user exceeds the first threshold, and
the imaging controller instructs the imaging terminal device to erase the imaging data that has already been recorded in a case where the second judgment device judges that the value of the body motion of the user does not exceed the second threshold.

13. The monitoring system of claim 10, wherein the imaging controller is configured to instruct the imaging terminal device that has started capturing an image of the user and recording imaging data in advance to erase the imaging data that has already been recorded in a case where the occurrence of the abnormality is not detected by the data analyzer.

14. A method comprising: acquiring information on an activity of a user, wherein the information on the activity of the user includes an acceleration of the user; analyzing the acquired information on the activity of the user and detecting occurrence of an abnormality in the activity of the user, wherein analyzing the acquired information further comprises:
calculating a posture of the user by determining inclination angles of the user's upper body from the acceleration of the user; calculating body motion of the user by: determining a norm of the acceleration values over a predetermined time period, and applying a filter to the norm of the acceleration values to obtain a filtered body motion value; determining whether the calculated posture transitions from a first posture to a second posture within a first time period; determining whether the filtered body motion value exceeds a threshold within a second time period following the posture transition; determining that the abnormality has occurred when the posture transition is detected followed by the filtered body motion value exceeding the threshold within the second time period; instructing an imaging terminal device that captures an image of the activity of the user to start capturing an image of the user and record imaging data in a case where the occurrence of the abnormality is detected; acquiring the imaging data recorded by the imaging terminal device; storing the acquired imaging data in a data storage device; and
outputting the imaging data, wherein the posture of the user comprises:
calculating a first inclination angle (θ) of a Z-axis of an acceleration sensor worn by the user with respect to a vertical direction and calculating a second inclination angle (φ) of an X-axis of the acceleration sensor with respect to the vertical direction, wherein the first posture is a supine posture and the second posture is an upright posture; the supine posture is determined when either: (a) 130°≤φ≤230° and −40°≤θ<30°, or (b) 130°≤φ≤230° and 140°<θ<220° and the upright posture is determined when 30°≤θ<140°.

15. The method according to claim 14, further comprising: instructing the imaging terminal device that has started capturing an image of the user and recording imaging data in advance to erase the imaging data that has already been recorded in a case where the occurrence of the abnormality is not detected.

16. The method according to claim 14, further comprising: determining a time of day when the abnormality is detected; and not acquiring the imaging data if the determined time of day is within a predetermined time slot when it is not necessary to monitor the user's activity.

* * * * *